(12) United States Patent
Deichmann et al.

(10) Patent No.: US 9,336,336 B2
(45) Date of Patent: May 10, 2016

(54) 2D IMAGE ARRANGEMENT

(75) Inventors: Nikolaj Deichmann, Copenhagen Ø (DK); Tais Clausen, Klagshamn (SE); Rune Fisker, Virum (DK); Henrik Öjelund, Lyngby (DK)

(73) Assignee: 3SHAPE A/S, Kobenhavn K (DK)

( * ) Notice: Subject to any disclaimer, the term of this patent is extended or adjusted under 35 U.S.C. 154(b) by 722 days.

(21) Appl. No.: 13/807,443

(22) PCT Filed: Jun. 29, 2011

(86) PCT No.: PCT/DK2011/050246
§ 371 (c)(1),
(2), (4) Date: Mar. 1, 2013

(87) PCT Pub. No.: WO2012/000511
PCT Pub. Date: Jan. 5, 2012

(65) Prior Publication Data
US 2013/0218530 A1     Aug. 22, 2013

Related U.S. Application Data

(60) Provisional application No. 61/359,454, filed on Jun. 29, 2010, provisional application No. 61/454,200, filed on Mar. 18, 2011.

(30) Foreign Application Priority Data

Jun. 29, 2010  (DK) ................................ 2010 00568
Mar. 18, 2011  (DK) ................................ 2011 00191

(51) Int. Cl.
*G06F 17/50*     (2006.01)
*A61C 13/00*     (2006.01)
(Continued)

(52) U.S. Cl.
CPC .............. *G06F 17/50* (2013.01); *A61C 9/0046* (2013.01); *A61C 13/0004* (2013.01); *A61B 1/0005* (2013.01)

(58) Field of Classification Search
CPC ..................................................... A61B 1/0005
USPC ............................................................ 703/13
See application file for complete search history.

(56) References Cited

U.S. PATENT DOCUMENTS 6,068,482 A    5/2000   Snow
6,261,248 B1   7/2001   Takaishi et al.
(Continued)

FOREIGN PATENT DOCUMENTS

EP     1 124 487 A1    8/2001
EP     1 124 487 B1    5/2007
(Continued)

OTHER PUBLICATIONS

An English Translation of the Office Action (Notice of Reasons for Rejection) issued on May 19, 2015, by the Japanese Patent Office in corresponding Japanese Patent Application No. 2013-517019. (2 pages).

(Continued)

*Primary Examiner* — Hugh Jones
(74) *Attorney, Agent, or Firm* — Buchanan Ingersoll & Rooney PC

(57) ABSTRACT

Disclosed is a method of designing a dental restoration for a patient, wherein the method includes providing one or more 2D images, where at least one 2D image includes at least one facial feature; providing a 3D virtual model of at least part of the patient's oral cavity; arranging at least one of the one or more 2D images relative to the 3D virtual model in a virtual 3D space such that the 2D image and the 3D virtual model are aligned when viewed from a viewpoint, whereby the 3D virtual model and the 2D image are both visualized in the 3D space; and modeling a restoration on the 3D virtual model, where the restoration is designed to fit the facial feature of the at least one 2D image.

30 Claims, 27 Drawing Sheets

(51) Int. Cl.
*A61C 9/00* (2006.01)
*A61B 1/00* (2006.01)

(56) References Cited

U.S. PATENT DOCUMENTS

| | | |
|---|---|---|
| 2003/0163291 A1 | 8/2003 | Jordan et al. |
| 2003/0169913 A1 | 9/2003 | Kopelman et al. |
| 2006/0127836 A1 | 6/2006 | Wen |
| 2010/0049351 A1 | 2/2010 | Monkmeyer |
| 2010/0076581 A1 | 3/2010 | Violante et al. |
| 2010/0145898 A1 | 6/2010 | Malfliet et al. |

FOREIGN PATENT DOCUMENTS

| | | |
|---|---|---|
| JP | 2002-528215 A | 9/2002 |
| JP | 2010-503437 A | 2/2010 |
| JP | 2010-524529 A | 7/2010 |
| WO | 00/25677 A1 | 5/2000 |
| WO | 2008/128700 A1 | 10/2008 |
| WO | WO 2008/128700 A1 | 10/2008 |
| WO | 2010/008435 A1 | 1/2010 |
| WO | WO 2010/008435 A1 | 1/2010 |
| WO | WO 2010/031404 | 3/2010 |

OTHER PUBLICATIONS

International Search Report (PCT/ISA/210) issued on Sep. 7, 2011, by the Denmark Patent Office as the International Searching Authority for International Application No. PCT/DK2011/050246, 3 pp.
Search Report issued by the Danish Patent and Trademark Office on Jan. 28, 2011, in the corresponding Danish Patent Application No. PA 2010 00568. (4 pages).
Notification of Transmittal of the International Search Report (Forms PCT/ISA/220 and PCT/ISA/210) and the Written Opinion of the International Searching Authority (Form PCT/ISA/237) dated Jul. 9, 2011, issued in corresponding International Application No. PCT/DK2011/050246. (11 pages).

Fig. 5B
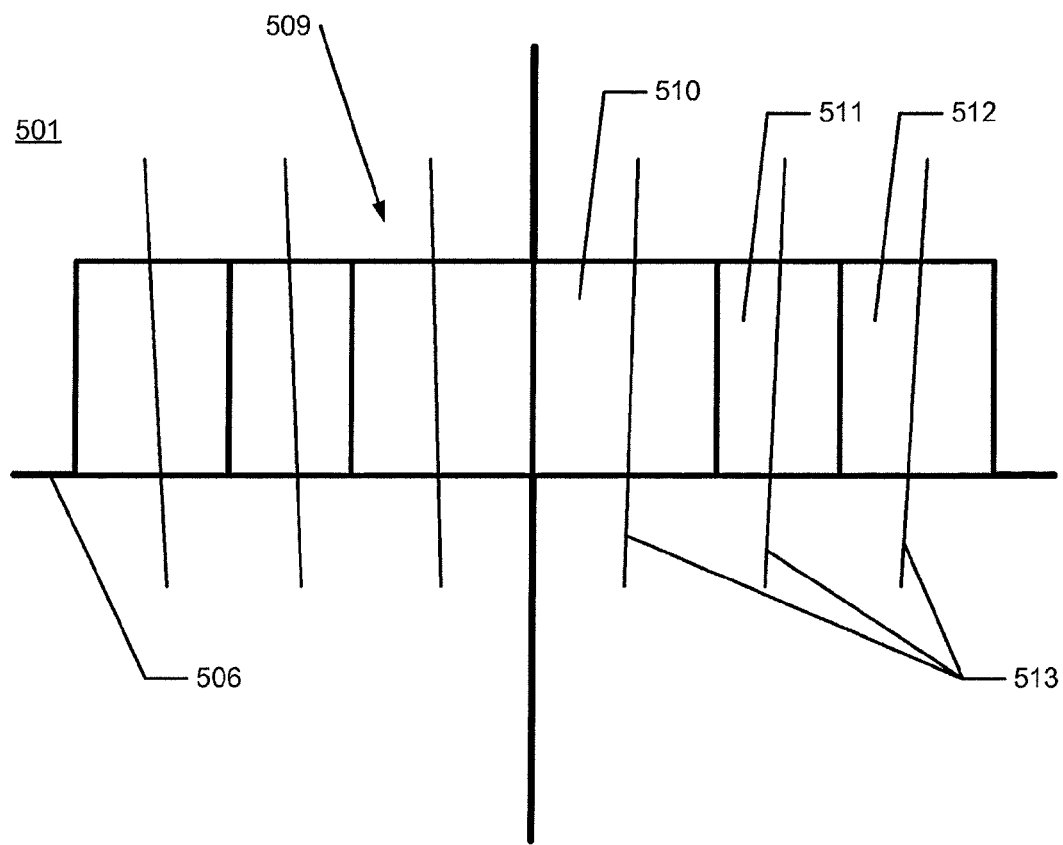
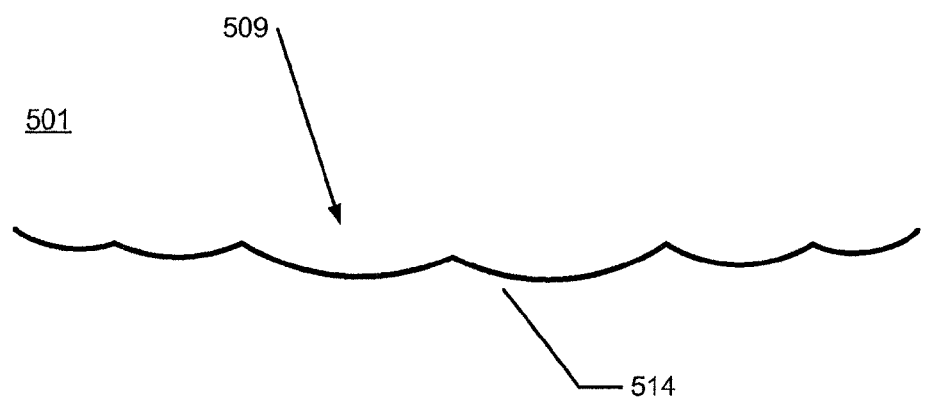
Fig. 5C

2D IMAGE ARRANGEMENT

FIELD OF THE INVENTION

This invention generally relates to a method of visualizing and modeling a set of teeth for a patient. More particularly, the invention relates to providing a 3D virtual model of the patient's set of teeth. The method is at least partly computer-implemented.

BACKGROUND OF THE INVENTION

Visualization and modeling or design of teeth are known in the field of dental restorations.

When a patient requires a dental restoration, such as crowns, bridges, abutments, or implants, the dentist will prepare the teeth e.g. a damaged tooth is grinded down to make a preparation where a crown is glued onto. An alternative treatment is to insert implants, such as titanium screws, into the jaw of the patient and mount crowns or bridges on the implants. After preparing the teeth or inserting an implant the dentist can make an impression of the upper jaw, the lower jaw and a bite registration or a single impression in a double-sided tray, also known as triple trays. The impressions are sent to the dental technicians who manufacture the restorations e.g. the bridge. The first step to manufacture the restoration is traditionally to cast the upper and lower dental models from impressions of the upper and the lower jaw, respectively. The models are usually made of gypsum and often aligned in a dental articulator using the bite registration to simulate the real bite and chewing motion. The dental technician builds up the dental restoration inside the articulator to ensure a nice visual appearance and bite functionality.

CAD technology for manufacturing dental restoration is rapidly expanding improving quality, reducing cost and facilitating the possibility to manufacture in attractive materials otherwise not available. The first step in the CAD manufacturing process is to create a 3-dimensional model of the patient's teeth. This is traditionally done by 3D scanning one or both of the dental gypsum models. The 3-dimensional replicas of the teeth are imported into a CAD program, where the entire dental restoration, such as a bridge substructure, is designed. The final restoration 3D design is then manufactured e.g. using a milling machine, 3D printer, rapid prototyping manufacturing or other manufacturing equipment. Accuracy requirements for the dental restorations are very high otherwise the dental restoration will not be visual appealing, fit onto the teeth, could cause pain or cause infections.

WO10031404A relates to tools in a system for the design of customized three-dimensional models of dental restorations for subsequent manufacturing, where the dental restorations are such as implant abutments, copings, crowns, wax-ups, and bridge frameworks. Moreover, the invention relates to a computer-readable medium for implementing such a system on a computer.

Visualizing and modeling teeth for a patient based are also known from the field of orthodontics.

US2006127836A discloses orthodontic systems and methods for determining movement of a tooth model from a first position to a second position by identifying one or more common features on the tooth model; detecting the position of the common features on the tooth model at the first position; detecting the position of the common features on the tooth model at the second position; and determining a difference between the position of each common feature at the first and second positions.

Thus orthodontics relates to movement of teeth, so the desired position of a tooth or teeth is determined, and based on the present position of that tooth or teeth, the movement from the present position to the desired position is determined. Thus within orthodontics the desired or resulting position of a tooth or teeth is/are is known before planning the steps of the movement.

It remains a problem to provide an improved method and system for providing esthetically beautiful and/or physiologically suitable results of modeling teeth, both within the field of restorations, implants, orthodontics etc.

SUMMARY

Disclosed is a method of designing a dental restoration for a patient, wherein the method comprises;
  providing one or more 2D images, where at least one 2D image comprises at least one facial feature;
  providing a 3D virtual model of at least part of the patient's oral cavity;
  arranging at least one of the one or more 2D images relative to the 3D virtual model in a virtual 3D space such that the 2D image and the 3D virtual model are aligned when viewed from a viewpoint, whereby the 3D virtual model and the 2D image are both visualized in the 3D space; and
  modeling a restoration on the 3D virtual model, where the restoration is designed to fit the facial feature of the at least one 2D image.

The terms designing and modeling are used interchangeably in this document to describe what is done to the restoration to make it fit to the patient. The user, e.g. a dental technician, may be digitally designing or modeling a restoration on the 3D virtual model.

It is an advantage that the 3D CAD modeling of the 3D virtual model is based on a 2D digital image, since the 2D image determines or indicates what kind of modeling is suitable, where the expression suitable may comprise physiologically suitable or esthetically suitable or appealing. Thus the 2D image is used to perform a correct modeling of the 3D model, since the 2D image functions as a benchmark or rule for what kind of modeling is possible or how the modeling can be with the limits provided by the 2D image. Thus the modeling of the 3D virtual model is decided and performed based on the one or more 2D image, i.e. such as that the modeling of the 3D virtual model is based on the visualization of the 2D image.

The patient's oral cavity may comprise at least the patient's present set of teeth, such as prepared teeth or unprepared teeth, if the patient is not toothless, and maybe part of the gums. If the patient is toothless, then the oral cavity may comprise the gums of the patient.

The 2D image(s) may typically be a digital image, and the term 2D digital image may be used interchangeably with the term 2D image in the specification.

It is an advantage that there may be one or more 2D images. If there are more 2D images, one 2D image may be used for alignment relative to the 3D virtual mode, and another 2D image may be used for designing the restoration. However, even if there are more 2D images, the same 2D image may be used both for alignment and for designing the restoration. The other 2D images may then just be used for visualization and presentation etc. If there is only one 2D image, that 2D image is used both for alignment with the 3D virtual model and for designing the restoration.

Thus the 2D image comprising the facial features may be denoted the first 2D image, and the 2D image which is used for alignment relative to the 3D virtual model may be denoted the second 2D image. If there is only one 2D image, then the first 2D image and the second 2D image is the same 2D image. If there are more 2D images, then the first 2D image and the second 2d image may be the same 2D image, but they may also be two different 2D images.

The restoration is configured to be manufactured, such as by rapid manufacturing, such as by milling, printing etc. The restoration may be veneered, such as by adding porcelain to the surface of it after machine manufacturing. When the restoration is finished, it may be inserted in the patient's mouth.

It is an advantage that the 2D digital image and the 3D virtual model are aligned when viewed from one viewpoint, since hereby the user or operator of the system performing the method, can view the 2D image and the 3D model from a viewpoint where they are aligned, since this enables and facilitates that modeling of the 3D model is based on the 2D image. That the 2D image and 3D model are aligned when seen from a viewpoint means that at least some structures of the 2D image and the 3D model are coinciding when seen from a viewpoint. Thus the 2D image and 3D model may not be aligned when seen from any viewpoint, thus there may be only one viewpoint from which the 2D image and the 3D model are aligned.

Furthermore, it is an advantage that the 2D image and the 3D model are arranged and remain as separate data representations which are not merged or fused together into one representation. By keeping the data representations as separate representations, time is saved and data processing time and capacity is reduced. Thus the 2D image is not superimposed or overlaid onto the 3D virtual model for creating one representation with all data included. Prior art documents describe that the data from e.g. a color image is added to the 3D model, such that the color content from the image is transferred to the 3D model, whereby the result is one representation, i.e. the 3D model including color. Creating such models requires more time and exhaustive data processing.

Thus, it is an advantage that the present method may be performed faster than prior art methods.

The method is for use when modeling teeth, but can of course also with advantage be used by students within the dental field when learning how to model teeth and what to take into consideration when modeling teeth.

Modeling of teeth is defined as comprising modeling of one or more dental restorations, modeling of one or more implants, modeling orthodontic movement of one or more teeth, modeling one or more teeth in a denture, e.g. a fixed or removable denture, to provide a visually pleasing appearance of the set of teeth etc.

Thus the modeling may comprise modeling of restorations, orthodontic planning and/or treatment, modeling of implants, modeling of dentures etc. When the CAD modeling comprises for example restorations, the virtually modeled restorations, such as crowns and bridges, can be manufactured by means of CAM, and the manufactured restorations can then eventually be inserted onto the patient's teeth by a dentist.

Arranging, placing, or positioning the 2D digital image on the 3D virtual model is performed digitally on a computer and shown on a user interface such as a screen, such that the user or operator obtains a visual representation of the 2D image and the 3D model together in the same field of view, whereby the operator can perform the modeling based on the simultaneous view of the 2D image and the 3D model instead of based on either one combined representation or separate views of the 2D image and/or the 3D model.

For facilitating the arrangement of the 2D image and the 3D model relative to each other, edge detection may be performed, whereby the contour of the teeth on the 2D image and/or on the 3D model is automatically derived. Edge detection can be performed by means of a software algorithm. Edges are points where there is a boundary or edge between to image regions, and edges can thus be defined as sets of points in the image which have a strong gradient magnitude. The contour of the teeth may thus be detected by detecting the edge between image portions showing the teeth and the gingival.

One or more 2D images may be provided in the method, and the 2D images may e.g. show the patient's face from different directions, show different parts of the patient's face, such as facial features in the form of the lips and the eyes or nose for example for determining facial lines, show different examples of new teeth which the teeth of the 3D model can be modeled to look like, show the patient's teeth before preparing the teeth for restorations and after preparing the teeth, etc.

In some embodiments the restoration is designed on at least one prepared tooth in the 3D virtual model.

In some embodiments the 2D image and the 3D model are aligned based on one or more unprepared teeth.

In some embodiments the prepared tooth in the 3D virtual model is a physical preparation of the patient's teeth.

In some embodiments the prepared tooth in the 3D virtual model is a virtual preparation modeled on the 3D virtual model.

In some embodiments the 3D virtual model comprises at least one prepared tooth.

In some embodiments the 3D virtual model comprises no prepared teeth, and where the 3D virtual model is of the patient's oral cavity before at least one tooth is prepared.

In some embodiments the method comprises providing two 3D virtual models, where the first 3D virtual model comprises at least one prepared tooth and the second 3D virtual model comprises no prepared teeth, and where the first and the second 3D virtual models are aligned.

In some embodiments the 2D image and the second 3D virtual model comprising no prepared teeth are aligned.

In some embodiments the 2D image and the first 3D virtual model comprising at least one prepared tooth are aligned based on the alignment between the first and the second 3D virtual model and based on the alignment between the 2D image and the second 3D model.

When aligning the 2D image and the 3D model, the 2D image may be of the patient's unprepared teeth, since it may be easier to align the 2D image and the 3D model, when the teeth on the 2D image are unprepared. When modeling the restoration e.g. new teeth of the 3D model, the 2D image may then be of the patient's prepared teeth, since e.g. restorations normally are modeled after having prepared the teeth by cutting part of the teeth such that crowns etc. can be attached to the prepared part of the teeth.

The 2D image of the prepared teeth may be aligned to the 2D image of the unprepared teeth before the restoration on the 3D model is designed/modeled based on the 2D image with the prepared teeth, since it may be easier to align the 2D images of the prepared and unprepared teeth, e.g. using the lips and other features of the face or teeth, than to align the 2D image of the prepared teeth with the 3D model, since here it may be difficult to find corresponding features on these.

However, the method may also be used before the dentist prepares any tooth or teeth, e.g. for presenting and showing the patient how his set of teeth may look if a restoration is made on one or more of the teeth.

The method may be used for designing a diagnostic wax-up used to visualize the results of a restoration prior to the treatment being executed.

When designing a diagnostic wax-up, a virtual margin line and a virtual preparation may be made for designing the diagnostic wax-up, even though no real preparation is made.

The method may be used for designing a temporary, which the patient can wear after the dentist has prepared a tooth and before the final restoration is manufactured and placed on the prepared tooth.

The restoration may be designed, e.g. automatically, by selecting a tooth in the 2D image, e.g. the tooth in the position where the restoration should be placed or a different aesthetic tooth. In the 2D image the selected tooth is only seen from one viewpoint, so only the front side, the width and the height of the tooth may be seen in the 2D image. Thus the backside of the tooth cannot be seen. A standard model tooth may be selected from a library, and this model tooth may be shaped as the selected tooth in the 2D image. The model tooth or restoration can only be shaped as the selected tooth in the surfaces which are seen in the 2D image. The rest of the model tooth or restoration may be shaped according to some standard for a tooth in that respective location in a mouth. E.g. the backside or the distal surface of a central tooth may typically be flat, whereas the distal surface of a canine may typically be triangularly shaped, and the distal surface of a molar may typically resemble the mesial surface of the tooth. Or the distal surface of the neighbor teeth or the corresponding tooth on the other side of the midline in the mouth may be used to shape the surfaces of the restoration which cannot be derived from the 2D image. The restoration can be designed on the 3D virtual model, and the part of the restoration which is in contact with e.g. the preparation may be automatically designed to resemble the shape of the restoration.

The restoration can be a crown, a bridge, an abutment, an implant, a denture, such as a fixed or removable denture, a full denture or partial denture, a diagnostic wax-up, a temporary etc.

Designing a restoration may comprise designing at least part of a preparation, designing at least a part of the gingival surrounding the restoration in the patient's mouth etc.

It is an advantage that the restoration is designed to fit or match the facial feature of the at least one 2D image, since this will provide a restoration which looks natural relative to the patient's face and/or this will provide a restoration which is aesthetic, such as symmetrical. The dental technical rules for designing teeth, mathematical or algorithmic rules and/or rules for aesthetics may be programmed into the software or used in the software or method for designing the restoration to fit the facial features, and based on these rules the restoration may be designed, e.g. partly automatically. The dental technician or the dentist may use his/her experience and knowledge about dental aesthetics and rules to design and determine when the restoration fits the facial feature in the patient's image or in a template or standard image of a face.

Designing the restoration to fit the facial features of the 2D image may be based on purely objective rules for restoration design. However designing the restoration to fit the facial features of the 2D image may alternatively and/or additionally be based on more subjective opinions and choices of the dental technician or dentist.

In some embodiments facial features are present in an image of the patient and/or in a generic image of a person.

In some embodiments the facial feature is one or two lips, one or more teeth, and/or the shape and/or size of the face.

In some embodiments the facial features comprise one or more imaginary lines of a face adapted to be detected in the 2D image, such as the midline, the horizontal line, and/or the bi-pupillar line.

If the 2D image is an image of at least part of the patient's face, then the facial features used for designing the restoration may be the lips of the patient, the smile line of the patient's mouth, the symmetry lines in the patient's face, the midline of the patient's face, the horizontal line of the patient's face, the patient's anterior teeth etc. Thus the restoration may be designed by fitting the restoration to the lips of the patient, by fitting the restoration to the smile line of the patient's mouth, by fitting the restoration to the patient's anterior teeth etc.

If the 2D image is an image, such as a drawing, of a generic template face, then the facial features used for designing the restoration may be symmetry lines of the template face, shapes and sizes of the teeth on the template face etc.

When designing the restoration to fit the facial features, the restoration may be designed such that there is a certain distance from the edge of the upper lip to the incisal edge of the anterior teeth, e.g. the centrals, when the patient smiles a natural smile; and/or such that a certain percentage or amount of the centrals are visible when the patient smiles.

Furthermore, when designing the restoration to fit the facial features, the restoration may be designed by considering the shape of the patient's face, the gender of the patient, the phenotypic characteristics of the patient, i.e. whether the patient is Asian, African, Caucasoid etc. For example Asians typically has smaller teeth, men typically have bigger teeth than women, oval teeth typically suit an oval face shape etc.

Furthermore, if the patient has a small dental arch or jaw, then the distance between the canines will typically be smaller, and the anterior teeth should then typically be more narrow, than the teeth in a patient with a large arch and a larger distance between the canines.

In some embodiments the restoration is a crown, a bridge, an abutment, an implant, a denture, a diagnostic wax-up, and/or a temporary.

In some embodiments the designing of the restoration is performed to automatically fit the facial features of the at least one 2D digital image.

In some embodiments the restoration is designed by selecting a tooth in the 2D image, and modeling the restoration to have the same shape as the selected tooth.

In some embodiments the 3D virtual model is generated by scanning a physical model of the patient's teeth, by scanning an impression of the patient's teeth, and/or by performing a direct scanning of the patient's teeth. If the patient is toothless, then the gums, a model or an impression of the gums may be scanned for creating a 3D model of the oral cavity.

In 3D scanning the object is analyzed to collect data on its shape. The collected data can then be used to construct digital, three dimensional models. In 3D scanning usually a point cloud of geometric samples on the surface of the subject is created. These points can then be used to extrapolate the shape of the subject.

In some embodiments the one or more 2D digital image comprises a patient-specific image of at least part of the patient's face.

An advantage of this embodiment is that the modeling can be based on an image of the patient, such that the modeling is performed with respect to the facial features forming the look or appearance of the patient, or with respect to some, a few or a single, specific visual facial features of the patient, such as the lips.

In some embodiments the one or more 2D digital image comprises a generic image of at least part of a human face.

An advantage of this embodiment is that the modeling can be based on a generic image, whereby it is not patient-specific facial features which determine the modeling, but instead it is a general image, e.g. the facial features may be some visually pleasing teeth from another person, or the facial feature may be a drawing of some ideal teeth etc.

In some embodiments the one or more 2D digital image is retrieved from a library comprising a number of images of teeth.

An advantage of this embodiment is that the 2D image, such as a generic image, can be selected from a library which contains for example several images of teeth, so that the patient e.g. can choose his/her desired new set of teeth from the library. The library may be a so called smile guide library comprising images of teeth and/or mouths which are shown while smiling, since visually pleasing teeth may be most important when smiling, since this may be when most teeth are shown to the surroundings.

The images of teeth in the library may be photos of teeth, may be drawings of teeth, etc. and thus the facial features are then teeth.

In some embodiments the 2D image comprises a cross for providing a visual symmetry which is adapted to be used for designing the restoration.

In some embodiments the one or more 2D digital image is a template for supporting designing the patient's teeth.

An advantage of this embodiment is that when the 2D image is a template, then the operator can arrange and model teeth using this template for obtaining a visually pleasing result of the modeling. Thus the template may comprise facial features in the form of guiding lines, rough blocks for arranging the teeth etc.

Thus facial feature, such as imaginary lines, in a patient's face, such as the midline, the horizontal line, the bi-pupillar line etc. may be used to determine how the restored teeth should look, i.e. the features, such as lines, may be used for designing the restoration(s).

In some embodiments the template comprises a facial feature in the form of the midline of a face.

In some embodiments the template comprises a facial feature in the form of horizontal line passing along the anterior teeth.

In some embodiments the template comprises a facial feature in the form of the occlusal plane of a face.

An advantage of the embodiments where the template comprises some facial feature, such as the midline of the face, a horizontal line, an occlusal plane etc, is that these features may assist in both arranging the 2D image and the 3D model relative to each other and in modeling of the restoration of the 3D model.

In some embodiments the template comprises a facial feature in the form of boxes adapted to fit the centrals, the laterals and the cuspids.

An advantage of this embodiment is that it enables the operator to easily model a restoration of the different anterior teeth to be visually pleasing. For example the laterals can with advantage be ⅔ of the width of the centrals, and the cuspids or canines can with advantage be slightly narrower than the centrals.

In some embodiments the template comprises a facial feature in the form of one or more long axes of anterior teeth.

An advantage of this embodiment is that the long axes can be used for indicating the long axis alignment of teeth and/or the vertical direction of teeth for support in modeling the restoration.

In some embodiments the facial feature in the form of the long axes of at least the upper anterior teeth converge toward the incisal edge or biting edge.

An advantage of this embodiment is that it is visually pleasing when the long axes of at least the upper anterior teeth converge toward the incisal.

In some embodiments the template comprises a facial feature in the form of a contour of teeth.

In some embodiments the contour comprises a shape of one or more teeth seen from the front.

An advantage of the embodiments relating to the contour of teeth is that using the visually pleasing contour of some suitable teeth may be a simple and easy way to model the restoration teeth of the 3D model.

In some embodiments the template comprises a facial feature in the form of a curve.

An advantage of this embodiment is that by means of a curve, distances and angles can be measured or viewed. For example a distance can be measured from the centre of the curve, and in one example the operator may measure x mm from a certain point on the curve, and at this distance something specific may be arranged, such as a distal point on a lateral. Furthermore the curve may be a symmetry curve for ensuring that the modeled restoration teeth will be symmetric.

In some embodiments the facial feature in the form of the curve comprises an arch following the upper and/or lower anterior teeth seen from the front or from above.

In some embodiments the facial feature in the form of the curve comprises a smile line adapted to follow the lower lip in a natural smile and the incisal edges of the upper teeth.

In some embodiments the template comprises a facial feature in the form of one or more curves for indicating the position of the gingival tissue.

An advantage of these embodiments relating to curves of the teeth and/or of the mouth and lips is that using some kind of curve(s) may be a simple and easy way to model the restoration teeth of the 3D model.

In some embodiments the one or more 2D digital image shows at least a number of front teeth.

It is an advantage to have a facial feature in the form of front teeth, since front teeth may be good starting points for designing other restoration teeth.

In some embodiments the one or more 2D digital image is a photograph showing at least a facial feature in the form of the patient's lips and teeth seen from the front.

An advantage of this embodiment is that when the 2D image shows the patient's lips and existing teeth, then the modeling of the restoration teeth can be performed such that they suit the patient's lips and unchanged teeth providing a visually pleasing result of the modeling.

In some embodiments the method further comprises virtually cutting at least a part of the teeth out of the one or more 2D digital image, if the 2D image comprises teeth, such that at least the lips remains to be visible in the 2D digital image.

An advantage of this embodiment is that when the lips and no or only some teeth are visible in the 2D image then it is easy to visualize the modeled restoration teeth of the 3D virtual model with the patient's lips and determine whether the restoration it is a good result of modeling. The cutting of teeth out of the 2D image may be performed virtually or digitally such that the information in the 2D image relating to the teeth is removed, deleted, made invisible etc.

If there is free space between the teeth, such as between the upper and lower teeth in the 2D image, then this free space may also be removed from the 2D image, such that everything inside the edge of the lips is removed so that the 3D model can be seen within the edge of the lips. The lips themselves should preferably not be cut out, since the lips should preferably be seen while designing the restoration of the teeth, such that the restoration is designed to fit the patient's lips or the standard, template, model lips from a template 2D image.

Virtually cutting the teeth out of the 2D image may be performed by segmenting the lips and the teeth in the 2D image. Segmentation may be performed by that the dental technician manually draws with a digital drawing tool along the edge or lines of the lips and/or teeth, and thereby performs the segmentation. The segmentation may also be performed automatically by means of well-known image processing algorithms. The segmentation may also be performed by means of analyzing the color difference in the 2D image, and using the criteria that teeth are normally white/yellow or grey colored, and that lips are normally red/pink/flesh colored. The segmentation may also be performed by defining one or more lip models or teeth models and then digitally searching the 2D image for features which match the lip models and/or teeth models.

The edge of the lips can be marked by means of image processing tools, digital drawing tools, such as manual tools, semi-automatic tools, full-automatic tools, standard image processing tools, a combination of different drawings tools etc.

One of the 2D images may be a 2D image of the patient where the teeth can be seen behind the lips, e.g. where as much as possible of the teeth is seen, e.g. in an image where the patient smiles, such as his/her natural smile.

It may be an advantage that the patient's present teeth can be seen in the 2D image, since this may be used when designing the restoration. In particular, how the patient's present teeth and lips look or appear relative to each other when the patient smiles, may be used when designing the restoration.

Another one of the 2D images may be a 2D image of the patient where the teeth cannot be seen, e.g. where the lips are closed together.

In some embodiments the 3D virtual model is visible behind the lips.

An advantage of this embodiment is that when the 3D model can be seen behind the lips, then the modeling of the restoration teeth can be performed while viewing the lips for determining if the modeling is satisfactory.

In some embodiments the method comprises cutting out the part of the 2D image which is inside the edge of the lips.

In some embodiments the edge of the lips is marked on the 2D image.

In some embodiments the edge of the lips is marked manually by means of digital drawing tools.

In some embodiments the edge of lips is marked by means of a digital spline curve.

In some embodiments the edge of the lips is marked by means of semi-automatic drawings tools.

When a part from the 2D image and a part from the 3D virtual model should be viewed/seen/be presented at the same time, then for example the pixels relating to the lips in the 2D image may be selected for view and the pixels relating to the teeth in the 3D virtual model may be selected for view, and the 2D image and the 3D virtual model may be combined in view this way.

As an alternative to cutting out the teeth of the 2D image, the teeth in the 2D image can be made transparent such that the teeth in the 3D model can be seen in the place of the 2D image teeth. Providing the teeth in the 2D image to be transparent can be performed similar to the cutting, e.g. by selecting some pixels to be viewed and selecting other pixels not to be viewed.

In some embodiments the one or more 2D digital image shows the face of the patient such that facial features in the form of facial lines, such as the midline and the bi-pupillar line, are detectable.

An advantage of this embodiment is that facial lines determines the geometry of the patient's face, and for obtaining a visually pleasing result of modeling, the teeth should fit with this overall geometry.

In some embodiments the one or more 2D digital image is an X-ray image of the patient's teeth.

An advantage of this embodiment is that when using or applying an X-ray image of the patient's teeth, the entire teeth with roots under the gingival can be seen, and thus broken or weak teeth or roots can be detected. Hereby for example implants exerting force on the teeth and roots can be planned to be arranged to exert force on non-broken or strong teeth and teeth roots instead of on the broken and weak teeth and roots.

In some embodiments the method further comprises providing a 3D computed tomography scan of the patient's face for facilitating aligning the one or more 2D image and the 3D model and/or for modeling the 3D virtual model.

In some embodiments the one or more 2D digital image is a still image from a video recording.

In some embodiments the one or more 2D digital image is derived from a 3D face scan.

When the 3D face scan is seen on the screen it may be seen from a certain perspective thereby yielding a certain 2D projection of the 3D scan. Thus a 2D image may be derived from the 2D projection of the 3D face scan.

In some embodiments the method further comprises providing a 3D face scan of the patient for facilitating aligning the one or more 2D image and the 3D model and/or for modeling the 3D virtual model.

The 3D face scan may be provided by means of aligning and/or combining multiple sub-scans of the face, such as sub-scans from different angles. Furthermore, at least some of the sub-scans may be at least partly overlapping.

The face scan may also comprise texture, and at least a part of the sub-textures of at least part of the sub-scans may be color adjusted ad/or color interpolated, such as by texture weaving, to provide the texture of the 3D face scan or 3D model.

When performing a face scan of the patient, at least part of the patient's hair may be powdered with a reflective powder.

Furthermore, silhouettes from multiple sub-scans may be extruded and subsequently intersected to provide a visual hull approximation.

Texture, such as color, from the 2D image or a face scan may be mapped onto the 3D virtual model and/or mapped onto the restoration.

If the restoration resembles the original tooth which is being restored, then it may be an advantage to use the texture, e.g. color, from the 2D image. But if the restoration does not resemble the original tooth or if there is no original tooth, then the texture, e.g. color, from the 2D image may not be mapped to the restoration.

Mapping the texture, e.g. color, from the 2D image onto the 3D virtual model and/or the restoration may be an advantage for designing the restoration, since it may e.g. help in determining the color of the restoration and/or other textural features of the restoration.

The teeth and tissue, such as gingival, in the 3D model may be at least partially segmented. The segmentation may be provided by means of a computer implemented algorithm, such as a shortest path algorithm applied on a 3D matrix representing curvature of the tooth surface.

Segmentation may alternatively/additionally be at least partly based on color information in the 3D model.

In some embodiments a face scan of the patient provides a measure of the distance that the upper and/or lower lip moves when the patient smiles, and the distance is adapted to be used for measuring the ideal length of at least some of the teeth.

An advantage of this embodiment is that at least the length of the front teeth is important for the visual appearance of the teeth.

In some embodiments the method further comprises providing at least part of the one or more 2D digital image to be at least partly transparent, such that the 3D virtual model is visual through the 2D digital image.

Transparency may mean full transparency, e.g. meaning something is completely invisible, partial transparency or translucency, e.g. meaning that the graphics is partially transparent, e.g. like a colored glass. Partial transparency may be simulated at some level by mixing colors.

When the entire or a part from the 2D image and/or the entire or a part from the 3D virtual model should be transparent, then for example some of, such as every second, pixels in the 2D image may be selected for view and some of, such as every other second, pixels in the 3D virtual model may be selected for view, and the 2D image and the 3D virtual model may be combined in view this way, such that one of them or both become transparent, e.g. interchangeably transparent.

Fading may be obtained similar to transparency, e.g. by selecting certain pixels for view and other pixels not for view.

In some embodiments the one or more 2D digital image is adapted to be smoothly faded in and out of the view.

An advantage of this embodiment is that when smoothly fading the 2D image in and out of view this provides that the visualization of the 2D digital image changes from being entirely visible to be partly visible and then maybe invisible and vice versa. Hereby the 2D image can be viewed as the user wishes. The fading in-and-out may be gradual.

In some embodiments the method further comprises providing at least part of the 3D virtual model to be at least partly transparent, such that at least one of the one or more 2D digital images is visual through the 3D virtual model.

In some embodiments the method comprises fading the 3D model smoothly in and out of the view.

In some embodiments the 2D image and the 3D model are adapted to be alternately faded in and out of view.

In some embodiments the 2D image is adapted to be faded into view, when the 3D virtual model is faded out of view, and vice versa.

In some embodiments the 2D image and the 3D virtual model are adapted to faded in and out of view independently of each other.

In some embodiments the 3D virtual model comprises the patient's set of teeth.

In some embodiments the 2D image and the 3D virtual model are aligned by means of scaling, translating and/or rotating the 2D image and/or the 3D model relative to each other.

In some embodiments the view of the 2D image is fixed, and the 3D virtual model is scaled and/or translated and/or rotated relative to the 2D image.

In some embodiments the method comprises selecting a viewpoint of the 3D virtual model which provides an optimal fit to the 2D digital image.

In some embodiments the dental articulation of the upper and lower teeth in the 3D virtual model is adapted to be adjusted to resemble the articulation of the upper and lower teeth in the 2D image.

In some embodiments the method further comprises scaling the one or more 2D digital image and the 3D virtual model to show at least part of the teeth in the same size.

An advantage of this embodiment is that the 2D image and the 3D model should be shown in the same scale in order for optimally performing the modeling. The scaling may be an automatic modification of the size of e.g. the 3D virtual model to the size of the 2D digital image or vice versa. Alternatively, the scaling may be of both the 2D image and the 3D model to resize them to a predetermined scale.

In some embodiments the method further comprises aligning the one or more 2D digital image and the 3D virtual model.

An advantage of this embodiment is that when the 2D image and the 3D model are aligned then modeling of the restoration may be performed easier and with a better result. Alignment may be defined as the adjustment of an object in relation with another object, such that structures of the objects are coinciding. Thus common or alike structures of the 2D image and the 3D model may be aligned.

In some embodiments the silhouette of the biting edge of at least the upper anterior teeth on the one or more 2D image and on the 3D virtual model is used to perform the alignment of the 2D image and the 3D virtual model.

An advantage of this embodiment is that in many cases the biting edge of the upper anterior teeth are seen on both the 2D image and on the 3D model, and therefore this biting edge may be an advantageous physical point of alignment.

In some embodiments the method further comprises projecting the plane of the one or more 2D digital image to the 3D virtual model.

An advantage of this embodiment is that when projecting the plane of 2D image to the 3D model or to a plane of the 3D model, the 3D model and the 2D image can be viewed in the same plane which may be an advantage when modeling the restoration teeth. The viewing of the 3D model and the 2D image in the same plane may otherwise be complex.

In some embodiments the method further comprises changing the perspective view of the one or more 2D digital image and/or of the 3D virtual model to obtain the same perspective view.

An advantage of this embodiment is that modeling of the restoration may be facilitated when the 2D image and the 3D model can be seen in the same perspective view.

For aligning the 2D image and the 3D model, a 2D projection of the 3D model may be performed. The projection may be a perspective projection, a parallel projection such as an orthographic projection, etc. Corresponding points may be selected on the 2D image and the 3D model, a projection of the 3D model onto 2D space may be made, and the distance between the corresponding points on the 2D projected 3D model and the 2D image may be minimized until the location of the corresponding points are coincident or almost coincident. The location may be minimized by means of iteration, like in the iterative closest point (ICP) method for aligning 3D models.

In some embodiments the method further comprises de-warping the perspective view of the one or more 2D image for visually aligning the 2D image and the 3D virtual model.

De-warping may be used, if the 2D image of the patient's mouth is for example taken in an angle from above, below and/or from a side, but it is desired that the 2D image of the patient's mouth is seen from the front, since a front image may be easier to use when designing a restoration for the patient's teeth.

Warping or de-warping may be used for correcting image distortion. Warping or de-warping may comprise mapping points to points. This can be based mathematically on any function from (part of) the plane to the plane.

Thus an advantage of this embodiment is that when de-warping or correcting the perspective view of the 2D image, then the view is digitally manipulated, and hereby points on the perspective view of the 2D image can be mapped to points on the 3D model or its plane. After de-warping or correcting the perspective of the 2D image, the 3D model can be re-aligned, such that the 2D image and the 3D model are aligned again.

Thus de-warping may be performed by projecting the 2D image or the teeth from the 2D image onto the 3D virtual model. Since the 3D model may only comprises the teeth of the patient, a face model, such as the patient's own face or a generic face model, may be used to align the 2D image and the 3D virtual model. A new perspective view of the 3D virtual model may now be selected and a new 2D image can be derived from this. This new 2D image may be a corrected, undistorted version or view of the original distorted 2D image.

In some embodiments scaling, aligning, projecting to a plane, de-warping perspective and changing perspective are defined as virtual actions for arrangement or alignment.

In some embodiments one or more of the virtual actions for arrangement comprises rotations and translations left/right and back/forth of the one or more 2D digital image and/or of the 3D virtual model.

An advantage of this embodiment is that by providing rotations, translations etc. then different movements of the 2D image and/or of the 3D model may be performed for facilitating the scaling, aligning, perspective changing and ultimately for facilitating the modeling of the teeth.

In some embodiments the method further comprises the steps of:
detecting anatomical points on the teeth, where the anatomical points are present and detectable both on the one or more 2D digital image and the 3D virtual model, and
performing the virtual actions for arrangement based on these corresponding anatomical points.

An advantage of this embodiment is that using corresponding, common or mutual anatomical points on the 2D image and the 3D model may be an easy way to perform alignment of the 2D image and the 3D model, where after modeling of the restoration teeth can be performed.

For correctly aligning the 2D image and the 3D virtual model, the number of corresponding points on the 2D image and the 3D model may be similar to the number of degrees (DOF) of freedom for moving the 2D image and the 3D model relative to each other. The number of degrees of freedom may for example be seven; thus seven corresponding points may be required for performing a correct alignment of the 2D image and the 3D virtual model.

For calculating the number of degrees of freedom, a camera model may be estimated. The camera model may comprise a number of internal parameters and a number of external parameters. The internal parameters may be magnification, also known as enlargement or scaling, and perspective projection or distortion. The external parameters may be the placement and orientation of the camera relative to the object, e.g. the set of teeth.

The degrees of freedom may be translations in the three directions in space and rotations about the three axes in space.

For reducing the number of degrees of freedom, and thus e.g. for reducing the required number of corresponding points on the 2D image and the 3D model, it can be assumed that all the teeth lie in the same plane. Then the internal parameters should not comprise the perspective projection or distortion, but only the magnification. Thus a parallel projection may be assumed, and for example it can alternatively and/or additionally be assumed that the 2D image of a patient's face is captured exactly from the front.

If a patient's teeth are photographed from a distance of about 1 meter, which may typically be the case when photographing teeth for this method, then the assumption about parallel projection may be acceptable.

For some cases it may be a reasonable assumption that all teeth lie in the same plane, however in other cases this assumption may not be correct, and it may be difficult or even impossible to align the 2D image and the 3D virtual model using this assumption.

In practice, alignment may be performed by fixing the 2D image in position and then moving the 3D virtual model relative to the fixed 2D image by using e.g. a 3D motion controller, a 3D navigation device, a 6DOF device (six degrees of freedom) or a 3D mouse, such as a spaceball.

If the 3D virtual model can be reduced to a 2D model, then the 2D image and the 2D model may be aligned using three points, since the alignment may then comprise magnification or scaling, translation in one direction and rotation about one axis.

The difficult part of aligning a 2D image and a 3D virtual model may be performing the rotation, since translation and scaling or magnification may be more easy to perform.

Perspective projection can be activated in the software program where the restoration is designed, and when perspective projection is activated the 2D image and/or the 3D virtual model may comprise more depth.

Perspective may be a parameter which can be adjusted, activated, fixed etc. in the software program for performing the method.

In some embodiments at least one corresponding anatomical point is selected to perform the virtual actions for arrangement.

An advantage of this embodiment is that one common or mutual point on the 2D image and the 3D model may be sufficient for arranging the 2D image and the 3D model relative to each other. However in other cases the 2D image and the 3D model should be aligned using more points, such as two, three or four points. In general three points may be suitable. Four points can be used for performing an even better arrangement or for use in more difficult cases.

In some embodiments the method further comprises the steps of:
providing a virtual measurement bar, and
performing the virtual actions for arrangement of the one or more 2D digital image and/or of the 3D virtual model by means of adjustment to the virtual measurement bar.

An advantage of this embodiment is that it may be easy and fast to use a virtual measurement bar to perform the virtual actions for arrangement such as scaling, where the sizes of the 2D image and the 3D model are adjusted to correspond to each other.

In some embodiments the method further comprises that a user performs the virtual actions for arrangement of the one or more 2D digital image and/or of the 3D virtual model by means of eye measure.

An advantage of this embodiment is that just by using simple eye measure, the operator can very quickly and reliably perform the arrangement of the 2D image and the 3D model relative to each other or perform a rough starting point for a more detailed adjustment.

In some embodiments the anatomical points are upper and/or lower distal and/or mesial points on a number of specific anterior teeth.

An advantage of this embodiment is that anatomical point on the upper and/or lower distal and/or mesial parts of the anterior teeth are normally easy to detect both on the 2D image and on the 3D model.

In some embodiments the modeling of the 3D model is performed automatically based on the one or more 2D digital image.

An advantage of this embodiment is that the user does not need to perform any manual modeling of the 3D model on the screen, when the modeling can be performed fully automatic. However, typically if an automatic modeling takes place, then the user may check that the modeling is satisfying, and maybe perform small corrections to the modeling.

In some embodiments the method further comprises automatically selecting one or more 2D digital image which provides an optimal fit to or match with the 3D virtual model.

An advantage of this embodiment is that a 2D image with an optimal, good or the best match or fit to the 3D model can automatically be selected, and hereby a good result of modeling of the restoration can be obtained, and furthermore the time used for performing the modeling of the restoration can be reduced, since no person needs to spend time on looking through a larger number of 2D images. The 2D image may be selected from a library of 2D digital images, or from any source comprising a number of images of teeth and smiles. The library may comprise templates, photos, drawings etc with facial features.

In some embodiments the optimal fit or match is determined based on specific parameters for providing an esthetically, visually pleasing appearance.

An advantage of this embodiment is that the optimal, best or just a good match or fit can be determined based on different parameters, such as the present size of the patient's teeth, on the curves of the patient's present teeth set, etc. New teeth which are very big may not suit a person who used to have very small teeth or a person who has thin lips. Likewise a new teeth set with a strong composition may not suit a person who used to have a teeth set with a soft composition or a person who has full lips etc. So based on the present facial features such as structures, features, shapes etc. of the patient's teeth, new teeth which will look natural and suit the patient can be determined from e.g. a template library of photos, drawings etc.

In some embodiments the alignment of the at least one 2D image and the 3D model is performed automatically.

In some embodiments the 3D model and two or more of the 2D images are aligned relative to each other, when there are more than one 2D image.

In some embodiments the 3D model and each of the 2D images are aligned relative to each other.

It is an advantage that the 3D model is aligned specifically to each of the 2D images, such that if shifting between the different 2D images, the correct alignment of the 3D model relative to the selected 2D image may automatically be presented on the user interface.

In some embodiments the different alignments of the 3D model relative to the two or more 2D images are stored in a data storage.

In some embodiments the alignment of the 3D model and a specific 2D image is retrieved from the data storage, when the specific 2D image is selected for view.

In some embodiments two or more of the 2D images are 2D images of at least part of the patient's face seen from different directions.

In some embodiments the method further comprises sectioning at least two or more of the teeth in the 3D model and/or in the one or more 2D images.

In some embodiments the 2D image and the 3D model are adapted to be arranged and/or viewed from one or more perspective views.

The perspective views may be from the front, from behind, from the side, from above, from below, and any combination of these view. A visual or non-visual point e.g. a center point, a line e.g. a centerline or a region e.g. a center region in the 3D model and/or in the 2D image may determine the point of reference for the perspective views.

In some embodiments the method comprises determining an angle of one or more of the perspective views.

The angle may be the angle relative to a center point of the 2D image and/or the 3D model. The angle may be an angle relative to a horizontal plane, and/or a vertical plane etc which virtually intersects the teeth in the 2D image and/or in the 3D model.

In some embodiments the method comprises predefining an angle of one or more of the perspective views.

In some embodiments at least one of the one or more 2D image is from a video stream of 2D images.

In some embodiments the 2D images from the video stream are from different perspective views.

In some embodiments the 3D model is configured to be aligned relative to one or more 2D images in the video stream.

In some embodiments the alignment of the 3D model and one or more 2D images for one or more perspective view is performed by means of interpolation and/or extrapolation of other perspective views.

It is an advantage that already determined perspective views can be used for alignment of other perspective views. The perspective views may be present or arranged on a virtual trajectory or curve and/or on a virtual view point sphere. Thus if two perspective views are already determined, a third perspective view located between the two perspective views can be determined by extrapolation or interpolation and the 3D model and the 2D image can be aligned relative to this or based on this. The perspective views or angles may be provided by a shift in angles, view directions etc, and the shifts may be smooth and continuous or in discrete steps.

In some embodiments the method comprises zooming at least one of the one or more 2D images and the 3D model in/out of view.

In some embodiments the 2D image and the 3D virtual model are adapted to be zoomed in/out simultaneously.

It is an advantage that the 2D image and the 3D model can be zoomed in/out simultaneously, and/or jointly, and/or together, and/or concurrently, and/or synchronously. Thus the increase or decrease in the size of the 2D image and the 3D model may be similar when zooming, the 2D image and the 3D model may follow each other when zooming, and the center point or center region of the zoom may be coinciding in the 2D image and the 3D model.

In some embodiments the zooming in/out is configured to be performed from one or more perspective views.

In some embodiments the zooming in/out is configured to be performed from one or more predefined angles.

In some embodiments the predefined angles determine the perspective views.

In some embodiments the method comprises providing the predefined angles in discrete steps.

In some embodiments the method comprises providing the predefined angles in a continuous sequence.

In some embodiments the 2D image and the 3D model are snapped or locked together in their correct alignment.

It is an advantage that if for example the 2D image is seen from a side perspective, then the 2D image is automatically snapped or locked to the correct angle relative to the 3D model.

When the alignment of the 2D image and the 3D virtual model has been found, this alignment can be saved, and if the 2D image and the 3D model are then moved again relative to each other, the saved alignment can be used to snap or lock the 2D image and the 3D virtual together again the correct alignment.

In some embodiments the snapping together of the 2D image and the 3D model is performed automatically.

In some embodiments each of the one or more 2D images is configured to be snapped together with the 3D model in their correct alignment.

In some embodiments the 2D image and the 3D model are aligned based on one or more unprepared teeth, if unprepared teeth are present in the 3D model.

In some embodiments the 2D image and the 3D model are aligned based on the teeth in the upper jaw.

It is an advantage to align based on the upper teeth because these are typically the most visible teeth on a 2D image, in particular the front teeth in the upper jaw are normally most visible and the alignment may therefore be improved if these teeth are used for the alignment.

Alternatively and/or additionally the teeth in the lower jaw of the 3D model can also be moved e.g. downwards to obtain a suitable alignment.

In some embodiments the angle which the 3D model and the 2D image are seen from as default is determined by the perspective view of the 2D image. The angle can also be denoted view, view point, perspective view etc.

In some embodiments the angle of the 3D model and the 2D image is configured to adapt relative to the perspective view of the 2D image.

The angle can also be denoted view, view point, perspective view etc.

In some embodiments the view of the 3D model is configured to adapt to the perspective view of a second 2D image, if this second 2D image is replacing a first 2D image.

It is an advantage that the view may change automatically when a second 2D image is selected for view, alignment etc.

In some embodiments the method further comprises generating a 3D image by combining at least three of the 2D images.

In some embodiments the method further comprises rendering the 3D model. It is an advantage to perform rendering of the teeth in the 3D model, such as photo-realistic rendering, since hereby the 3D model is made to look more realistic and nicer. The 3D model may be for example yellow or gray by default, so by rendering the teeth in the 3D model to be for example more white, the 3D model teeth looks better and realistic.

The rendering can be performed by means of well-known methods performed using well-known computer programs.

In some embodiments the method further comprises providing textural features on the 3D model.

It is an advantage to provide textural features on the 3D model for making the teeth of the 3D model look more realistic and real. The textural features of the teeth may be obtained from a 2D image of the patient's existing teeth, the textural features may be from a standard template, may be generated specifically to the specific 3D model based on size, shape etc of the teeth. Furthermore, other parameters such as shadow, geometry, viewpoint, lighting, and shading information can be provided to the 3D model for making the teeth of the 3D model look more realistic and possibly look more esthetic.

In some embodiments texture from the 2D image is mapped onto the 3D virtual model and/or the restoration.

In some embodiments the rendering is a photo-realistic rendering.

In general it is an advantage of the method and the embodiments that it/they enable(s) dental laboratories (labs) to superimpose a patient's actual face and smile images in the design process and utilize that directly to produce optimally esthetic and personalized restorations. Labs can show the dentist's patients exactly how a new restoration will transform their smiles and get feedback. The smile visualization is highly realizable because it may be solidly backed by the manufacturable 3D model and not just 2D image manipulations.

Personalized designs with patient specific 2D-image overlays can be obtained by importing 2D images of the patient's lips, teeth and smile to design restorations that exactly suit the patient's personal look. Image manipulation tools may be applied to mask away the teeth, and alignment tools may be used to bring lips and new teeth design together as a perfect personalized design guide.

High esthetics with generic 2D-image overlays can be obtained by using 2D-image libraries that help in achieving high esthetics, even without pictures of the actual patient's smile. By means of the method it is possible to select from a variety of smile-guides and design-templates to recreate complete smile compositions to apply with the restoration design.

Before-and-after visualization can be obtained for example by continuously interchanging between situation views through gradual fading in-and-out, whereby technicians, dentists and patients are easily able to detect even the smallest alterations and smile details for optimal comparisons.

The present invention relates to different aspects including the method described above and in the following, and corresponding methods, devices, systems, uses and/or product means, each yielding one or more of the benefits and advantages described in connection with the first mentioned aspect, and each having one or more embodiments corresponding to the embodiments described in connection with the first mentioned aspect and/or disclosed in the appended claims.

In particular, disclosed herein is a system for designing a dental restoration for a patient, wherein the system comprises:
  means for providing one or more 2D images, where at least one 2D image comprises at least one facial feature;
  means for providing a 3D virtual model of at least part of the patient's oral cavity;
  means for arranging at least one of the one or more 2D images relative to the 3D virtual model in a virtual 3D space such that the 2D image and the 3D virtual model are aligned when viewed from a viewpoint, whereby the 3D virtual model and the 2D image are both visualized in the 3D space; and
  means for modeling a restoration on the 3D virtual model, where the restoration is designed to fit the facial feature of the at least one 2D image.

Furthermore the present invention relates to a computer program product comprising program code means for causing a data processing system to perform the above method, when said program code means are executed on the data processing system, and a computer program product according to the previous claim, comprising a computer-readable medium having stored there on the program code means.

According to another aspect, disclosed is a computer-implemented method of visualizing, designing and modeling a set of teeth for a patient, wherein the method comprises the steps of:
  providing one or more 2D digital images;
  providing a 3D virtual model of at least part of the patient's oral cavity;
  arranging at least one of the one or more 2D digital images relative to the 3D virtual model in a 3D space such that the at least one 2D digital image and the 3D virtual model are aligned when viewed from a viewpoint, whereby the 3D virtual model and the at least one 2D digital image are both visualized in the 3D space; and modeling the 3D virtual model based on at least one of the one or more 2D digital images.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIGS. 5A-5G show examples of 2D images as templates.

DETAILED DESCRIPTION

In the following description, reference is made to the accompanying figures, which show by way of illustration how the invention may be practiced.

Figure 1:
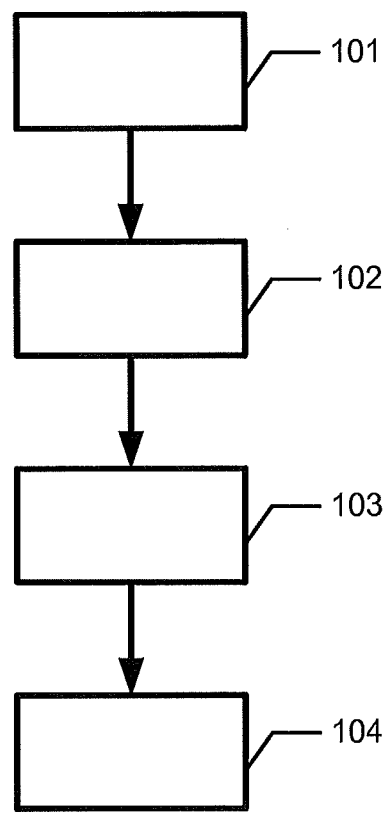
FIG. 1 shows an example of a flowchart of a method of visualizing and modeling a set of teeth for a patient.

FIG. 1 shows an example of a flowchart of a method of designing a dental restoration for a patient.

In step 101 one or more 2D digital images is provided, where at least one 2D image comprises at least one facial feature. The 2D image may be photograph of at least part of the patients face, a template of teeth, a drawing of teeth, a photo or image of an esthetic set of teeth etc. The 2D digital image may be shown on a user interface, such as a computer screen.

In step 102 a 3D virtual model of the patient's oral cavity comprising the patient's set of teeth, if there are any teeth, is provided. The 3D model of the patient's set of teeth may be generated by scanning a physical model of the patient's teeth, by scanning an impression of the patient's teeth, and/or by performing a direct scanning of the patient's teeth. If the patient is toothless, then the gums, a model or an impression of the gums may be scanned for creating a 3D model of the oral cavity. The 3D virtual model may be shown on a user interface, such as a computer screen.

In step 103 a 2D digital image is arranged or positioned relative to the 3D virtual model for visualizing the 3D virtual model relative to the 2D digital image. The arrangement or positioning is a digital, virtual arrangement, performed by means of software, such that the 2D image and the 3D model can be viewed together. The 2D digital image and the 3D virtual model are aligned when viewed from a viewpoint, whereby the 3D virtual model and the 2D digital image are both visualized in the 3D space. The user of the software program may use digital tools to manually align the 2D image and the 3D virtual model, or the 2D image and the 3D virtual model may automatically be aligned by means of digital processing means, or the alignment of the 2D image and the 3D virtual model may be a combination of manually alignment performed by the user and automatic alignment. The 2D image used for alignment with the 3D virtual may the same 2D image comprising facial features or it may be a different 2D image.

In step 104 a restoration of the 3D virtual model is modeled, where the restoration is designed to fit the facial feature of the at least one 2D image. Thus the part of the 3D virtual model of the patient's set of teeth comprising the restoration is digitally or virtually modeled or designed based on the visualization of the arrangement of the 2D image comprising the facial feature. Thus the 3D model of the patient's existing teeth is modeled using CAD, and the modeling may comprise restorations, orthodontic planning and/or treatment, prosthetics, removable dentures etc. The virtually modeled restorations, such as crowns and bridges, can be manufactured by means of CAM, and the manufactured restorations can then be inserted onto the patient's teeth by a dentist.

Figure 2A:
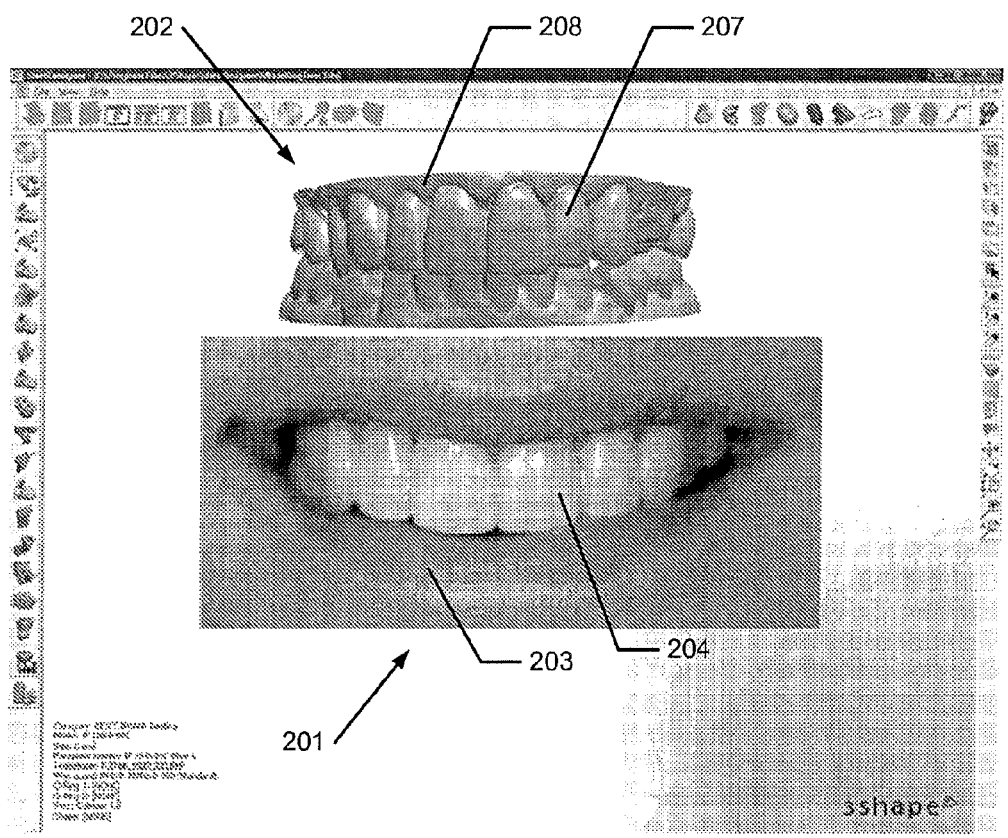
FIGS. 2A-2B show examples of visualizing a 2D image and a 3D model together.
Figure 2B:
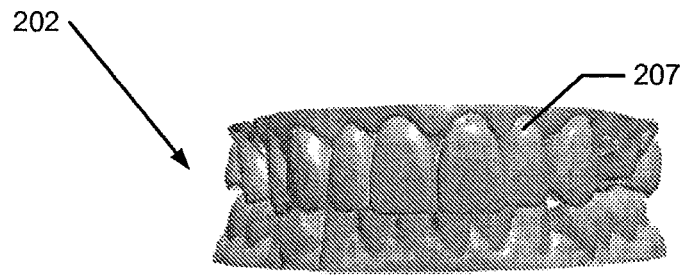
Figure 2B:
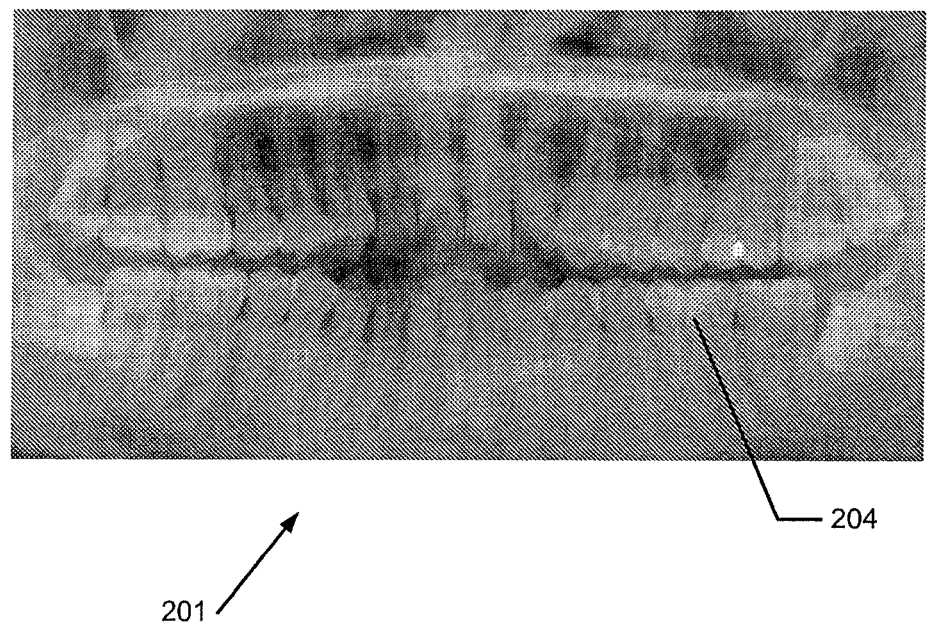

FIG. 2 shows examples of visualizing a 2D image and a 3D model together. FIG. 2a) shows a screen shot on which both a 2D image 201 and a 3D model 202 are seen simultaneously. The 2D image 201 is a photograph of a part of a person's face showing facial features in the form of the mouth with lips 203 and teeth 204 behind the lips 203. The photograph may be of the patient himself or of another person. Using a photograph of the patient may be advantageous if the patient's teeth have been broken and the patient then wishes to have his teeth restored to look like they did before the damage. Using a photograph of another person may be an option if the patient wishes to have his teeth restored, exchanged by a new teeth set and/or treated by orthodontics in order for them to look and/or be arranged differently than they do at present.

The 3D model 202 of the patient's teeth comprises gingival 208 and teeth 207.

FIG. 2b) shows an example where the 2D image 201 is an X-ray image of the patient's teeth. The X-ray image shows facial features in form of the teeth 204 of the patient. Since the X-ray image shows the teeth approximately on lines, i.e. not on curves as in real-life, at least part of the plane of the X-ray image may be changed with regard to the perspective, warped, projected and/or bended to be arranged relative to the 3D model 202 with teeth 207.

FIG. 3 shows an example of visualizing and arranging a 2D image and a 3D model.

Figure 3A:
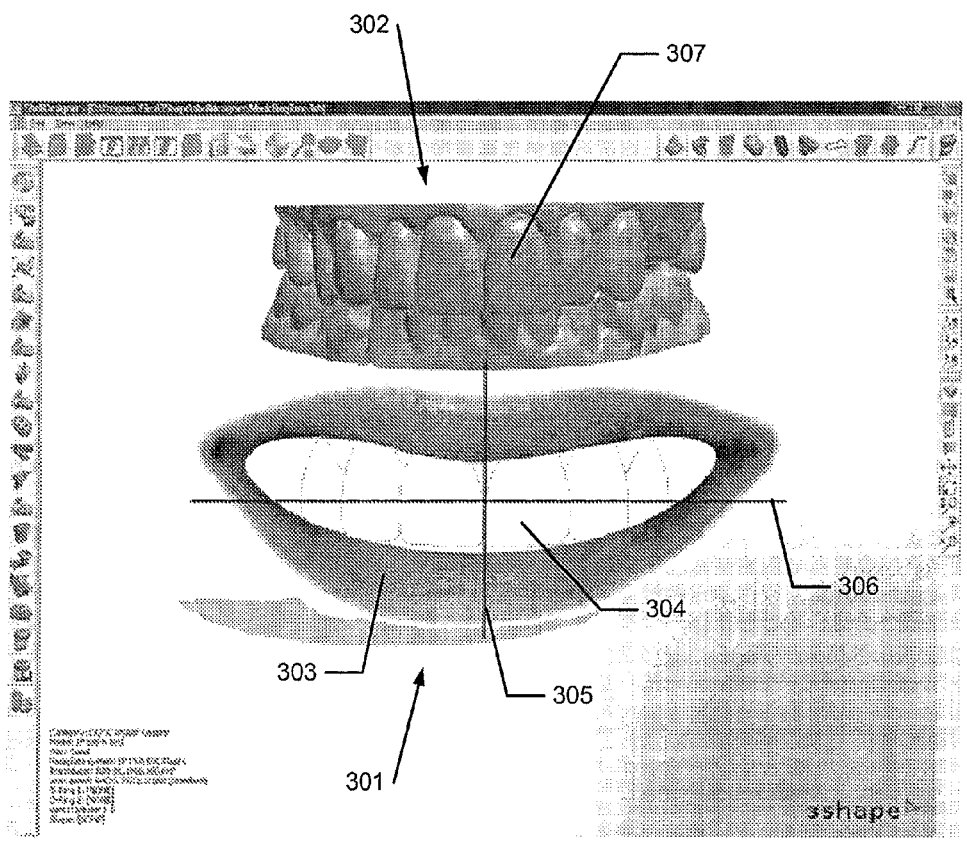
FIGS. 3A-3C show an example of visualizing and arranging a 2D image and a 3D model.

FIG. 3a) shows a screen shot on which both a 2D image 301 and a 3D model 302 of teeth are seen simultaneously. The 2D image 301 is a photograph or drawing showing facial features in form of a pair of lips 303 and an outline of teeth 304 behind the lips. A vertical line 305 and a horizontal line 306 are drawn through the 2D image 301, and they may also be used as guiding lines for modeling a restoration.

Figure 3B:
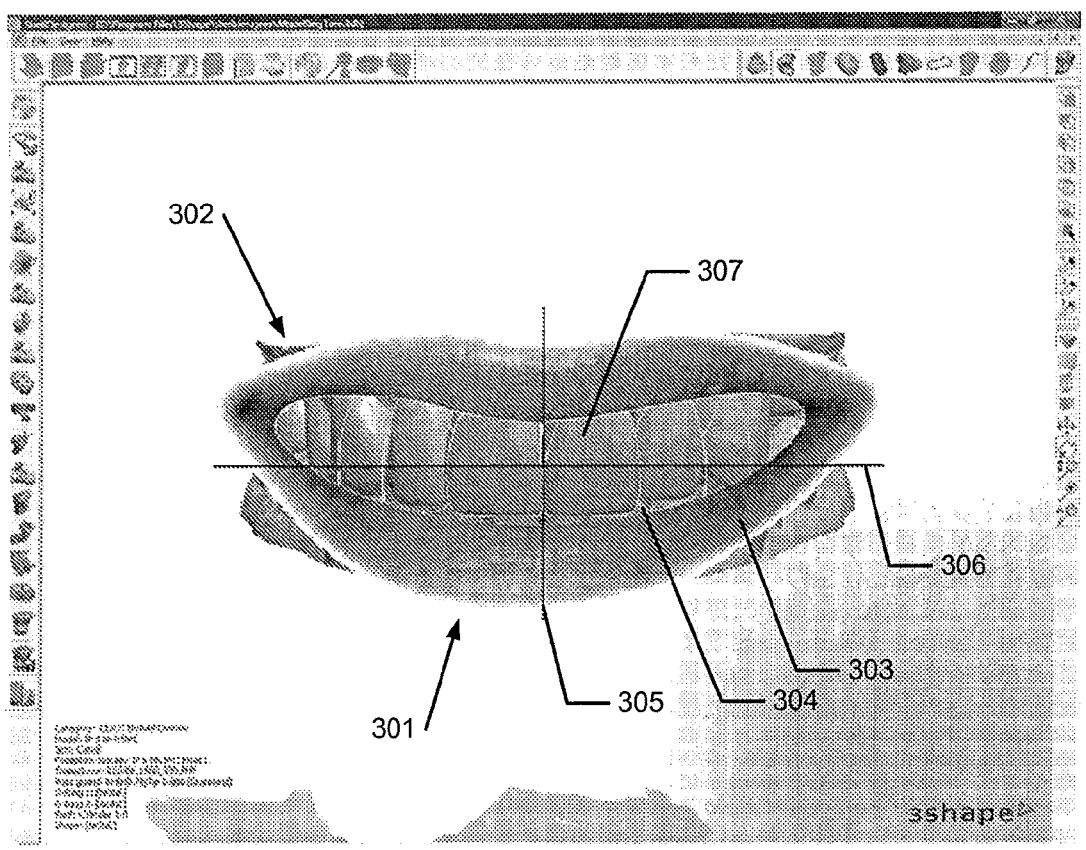

FIG. 3b) shows a screen shot on with the 2D image 301 is arranged and aligned relative to the 3D model 302. The teeth 307 of the 3D model 302 can be seen through and between the lips 303 and the outline of teeth 304 of the 2D image 301. When arranging and aligning the 2D image relative to the 3D model, modeling of a restoration on the 3D model is facilitated. The vertical line 305 and the horizontal line 306 are also seen in FIG. 3b).

Figure 3C:
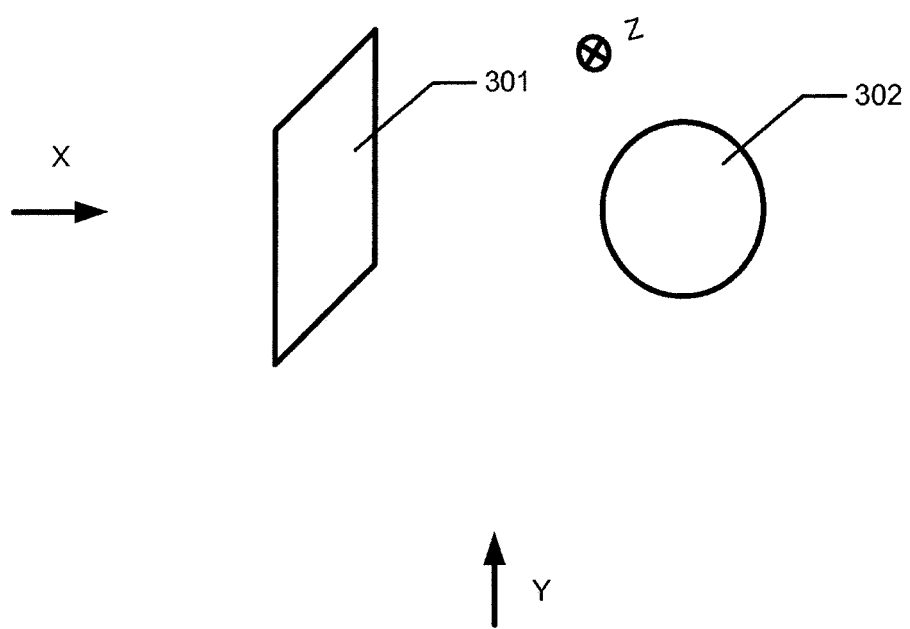

FIG. 3c) shows a sketch of a 2D image 301 and a 3D model 302 seen in a perspective side view illustrating alignment from a viewpoint.

The 2D image 301 and the 3D model are in this figure attempted to be drawn in a perspective side view to show that if the 2D image and the 3D model are viewed from this viewpoint then they are not aligned. In the other figures, e.g. FIG. 3b) the 2D image and the 3D model are viewed from a front viewpoint in which they are aligned. As seen there is a distance between the 2D image and the 3D model to indicate that the 2D image and the 3D model are separate representations and not one representation containing data from two representations. The distance can be any distance, such as shorter or longer than illustrated in the proportion here.

The arrow denoted X illustrates the front view in which the 2D image and the 3D model are aligned, as seen in e.g. FIG. 3b).

The arrow denoted Y illustrates a bottom view where the 2D image and the 3D model are viewed from below, and as can be derived from the figure, the 2D image and the 3D model are not aligned when viewed from the Y viewpoint.

The end of an arrow, circle with cross, denoted Z illustrates a side view, and as explained above with respect to the perspective side view, the 2D image and the 3D model are not aligned when viewed from this viewpoint.

Figure 4A:
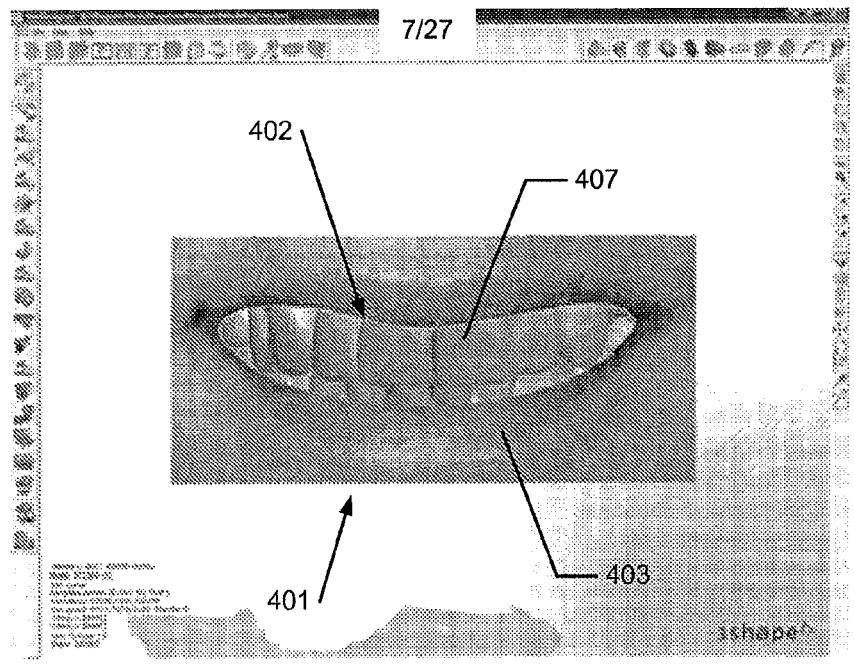
FIGS. 4A-4C show examples of arranging the 3D model and the 2D image relative to each other.
Figure 4B:
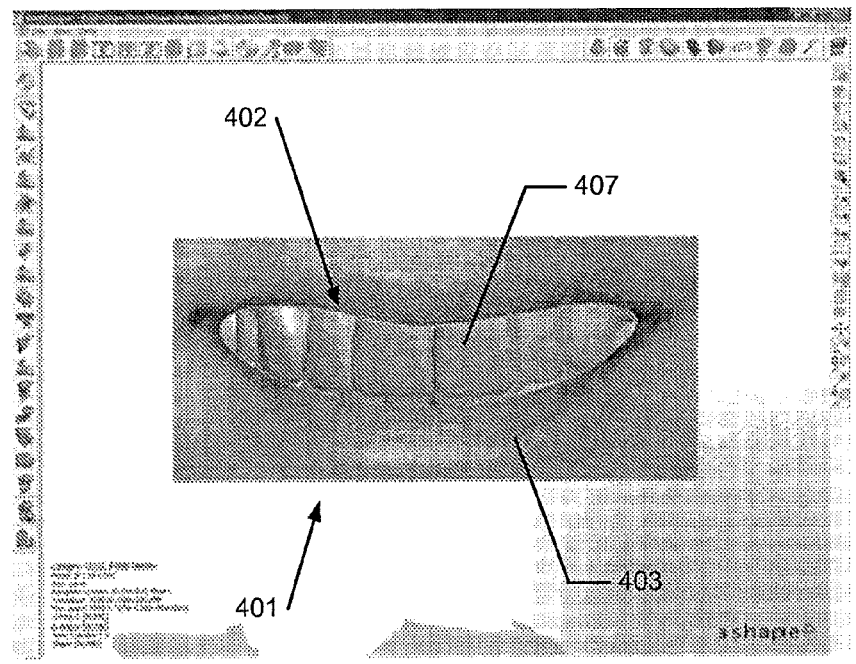
Figure 4C:
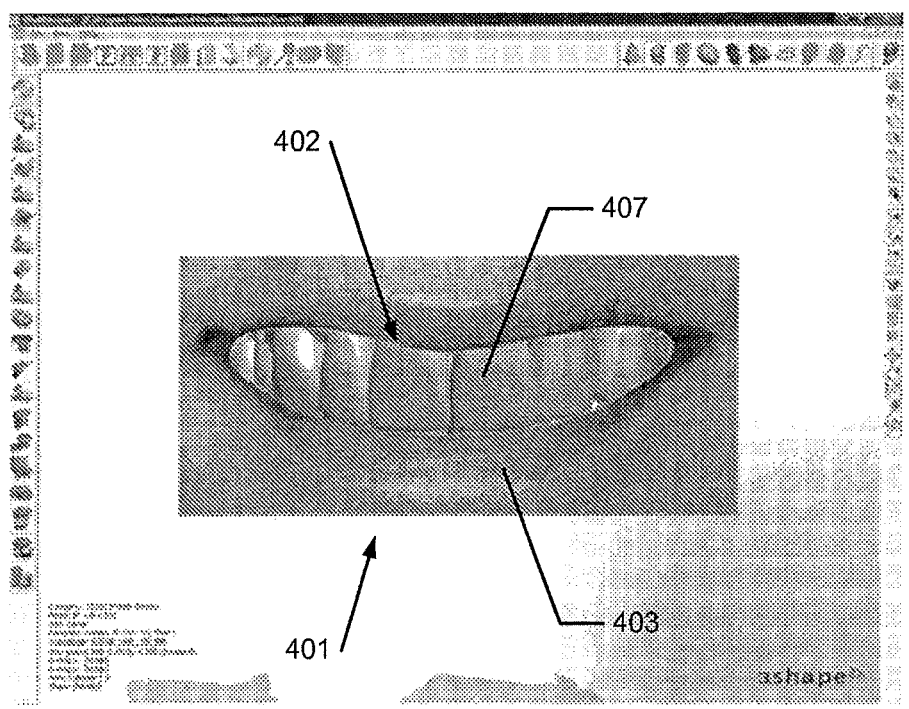

FIG. 4 shows examples of arranging the 3D model and the 2D image relative to each other.

FIGS. 4a), b) and c) show examples of different arrangements of the 3D model 402 relative to the 2D image 401. The teeth 407 of the 3D model 402 is seen to be moved relative to the lips 403 of the 2D image 401 in the FIGS. 4a), b) and c). When the arrangement of the 3D model 402 has become suitable relative to the 2D image 401, the actual modeling of the teeth 407 of the 3D model 402 may be performed.

FIG. 5 shows examples of 2D images as templates comprising facial features. FIG. 5a) shows an example of a 2D digital image 501, which is a reference frame for arranging the patient's teeth and/or modeling a restoration. The reference frame comprises a template 509 for the upper anterior or front teeth. The template 509 comprises facial features in the form of the midline of a face 505 and a horizontal line 506 passing along the incisal edge of the anterior teeth.

The template 509 comprises facial features in the form of boxes adapted to fit the centrals 510, the laterals 511 and the cuspids 512, also known as canines. The laterals 511 may ideally be ⅔ of the width of the centrals 510, and the cuspids 512 may ideally be slightly narrower than the centrals 510.

FIG. 5b) shows an example where the 2D image 501 is a template 509 comprising facial features in the form of the long axes 513 of the centrals 510, the laterals 511, and the cuspids 512. The long axes 513 converge toward the incisal edge indicated by the horizontal line 506.

FIG. 5c) shows an example where the 2D image 501 is a template 509 showing facial features in the form of a contour 514 of anterior or front teeth seen from the front.

Figure 5A:
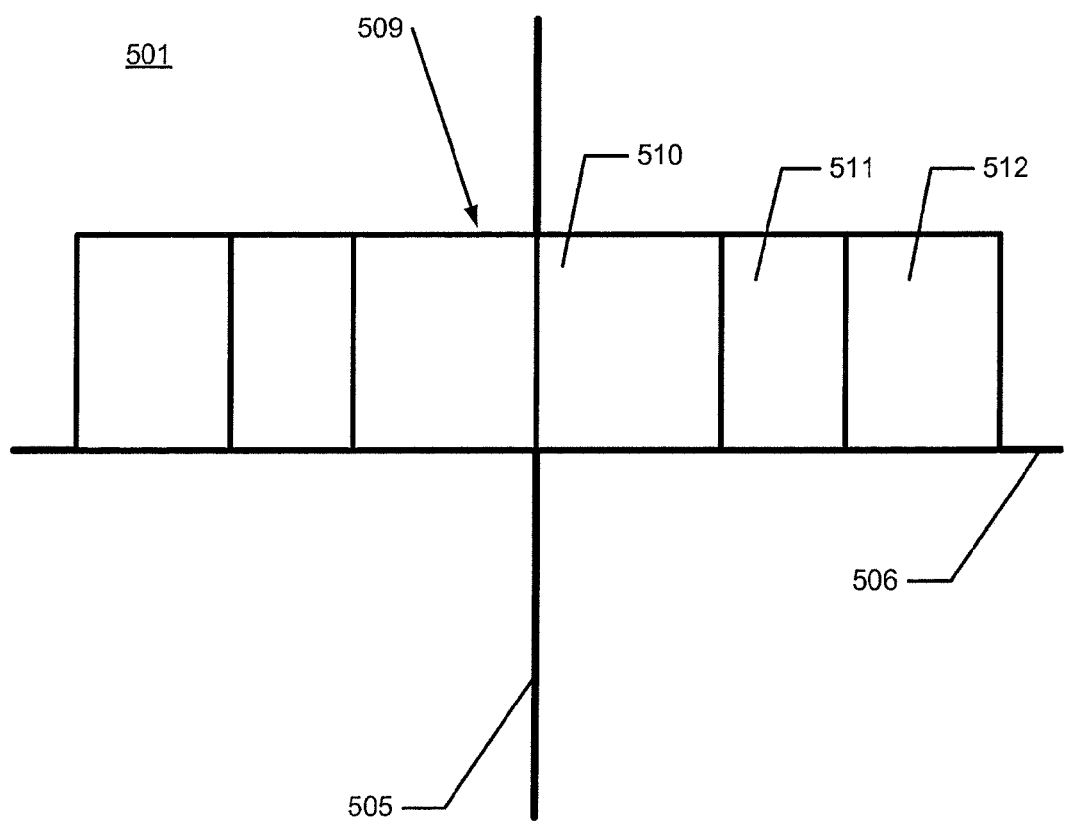
Figure 5D:
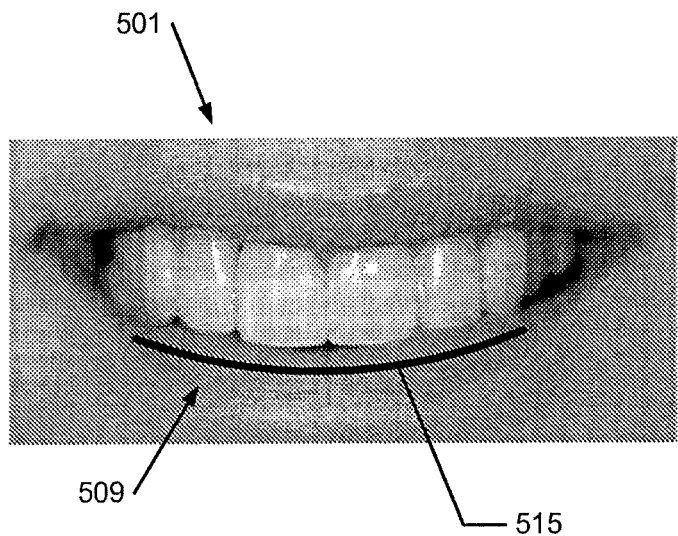

FIG. 5d) shows an example where the 2D image 501 comprises a template 509 comprising facial features in the form of a curve 515 of a smile line adapted to follow the lower lip in a natural smile and the incisal edges of the upper anterior teeth 510, 511, 512, as seen from the front.

Figure 5E:
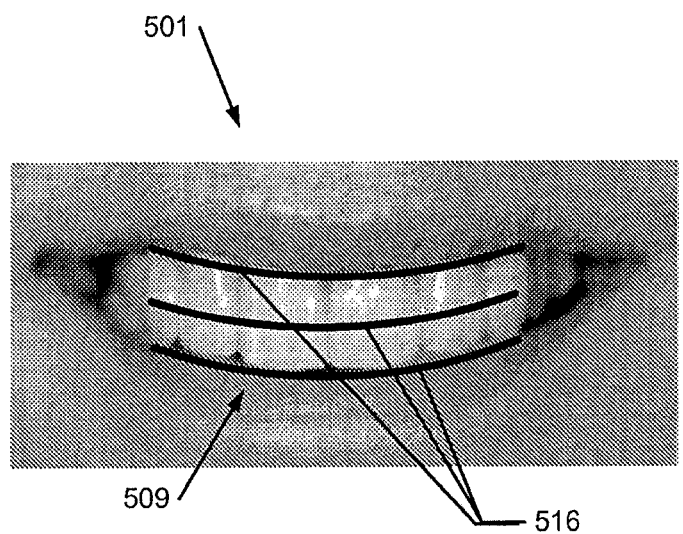

FIG. 5e) shows an example where the 2D image 501 comprises a template comprising facial features in the form of three curves 516 for indicating the position of the gingival tissue.

Figure 5F:
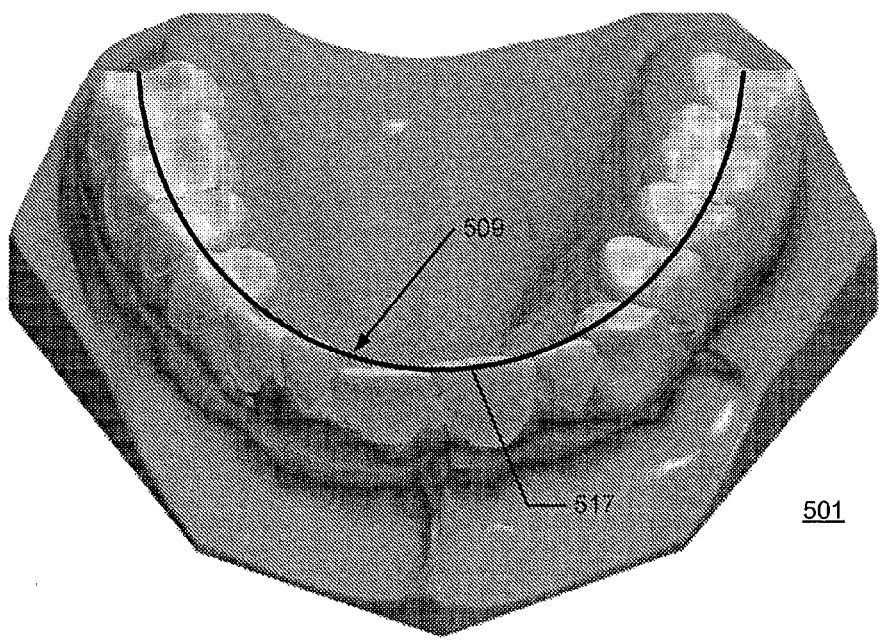

FIG. 5f) shows an example where the 2D image 501 comprises or is a template 509 comprising a curve in the form of an arch 517 which follows the upper teeth as seen from above.

Figure 5G:
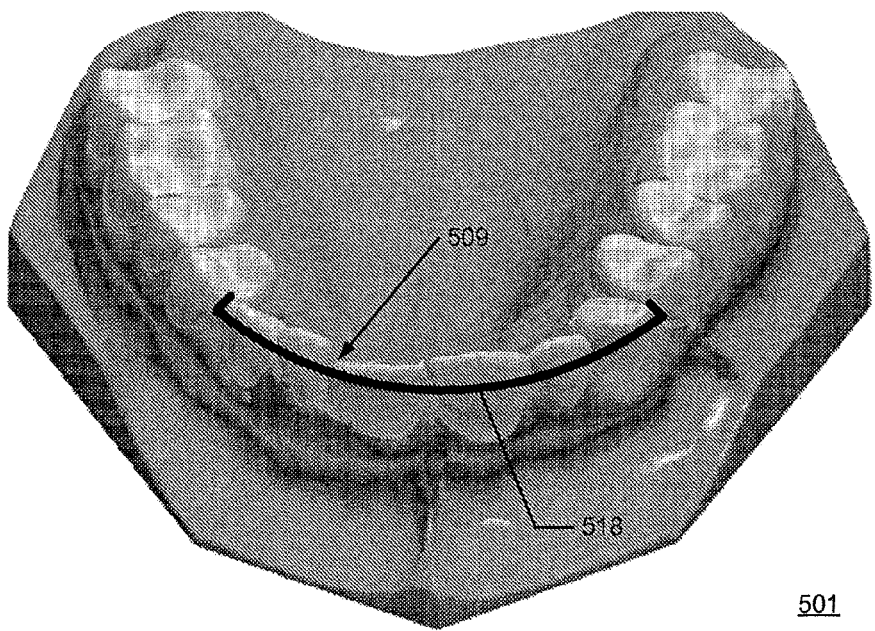

FIG. 5g) shows an example where the 2D image 501 comprises or is a template 509 comprising a curve 518 which follows the upper anterior teeth as seen from above.

The arch 517 and the curve 518 may also be denoted facial features.

FIG. 6 shows examples of how to perform alignment or virtual actions for arrangement of the 2D image and the 3D model relative to each other.

Virtual actions for arrangement can comprise the following:
  scaling the 2D digital image and the 3D virtual model to show at least part of the teeth in the same size on both of them;
  aligning the 2D digital image and the 3D virtual model;
  projecting the 3D virtual model to a/the plane of the 2D digital image;
  changing the perspective view of the 2D digital image and/or of the 3D virtual model to obtain the same perspective view for both of them when visualizing the positioning;
  de-warping the perspective view of the 3D virtual model for visually aligning the 2D image and the 3D virtual model.

The virtual actions for arrangement can be performed by means of rotations and translations to the left and right and back and forth of the 2D digital image and/or of the 3D virtual model.

In one example (not shown) the silhouette of the biting edge of at least the upper anterior teeth on the 2D image and on the 3D virtual model is used to perform the aligning of the 2D image and the 3D virtual model.

Figure 6A:
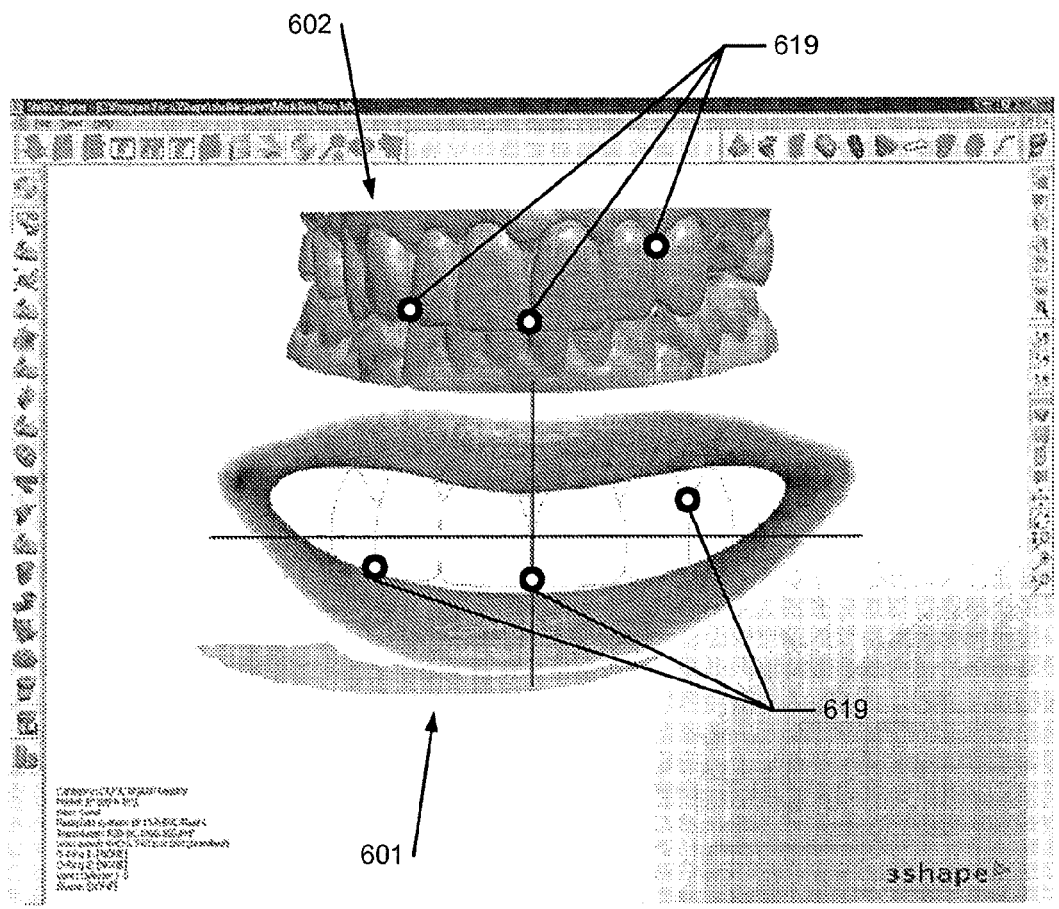
FIGS. 6A-6B show examples of how to perform virtual actions for arrangement of the 2D image and the 3D model.

FIG. 6a) shows an example where the alignment or a virtual action for arrangement such as alignment is performed using detected corresponding anatomical points 619 on the teeth on the 2D digital image 601 and on teeth on the 3D virtual model 602. The anatomical points 619 shown in FIG. 6a) are at the upper anterior teeth. One anatomical point is on the incisal edge at the distal side of the left lateral tooth, where left is left as seen in the figure, but right for the patient. Another anatomical point is on the incisal edge between the left and the right central teeth. The third anatomical point is at the gingival between the right lateral tooth and right cuspid tooth, where right is right as seen in the figure, but left for the patient.

When the corresponding anatomical points 619 are detected and e.g. marked as in the figure on both the 2D image 601 and the 3D model 602, the 2D image 601 and the 3D model 602 can be arranged relative to each other and aligned to each other by providing that the corresponding anatomical points 619 on the 2D image 610 and on the 3D model 602 cover, overlap, match or fit together. When corresponding anatomical points 619 are selected on the screen, the software may automatically arrange the 2D image 601 and the 3D model 602 such that the points 619 are overlapping.

Figure 6B:
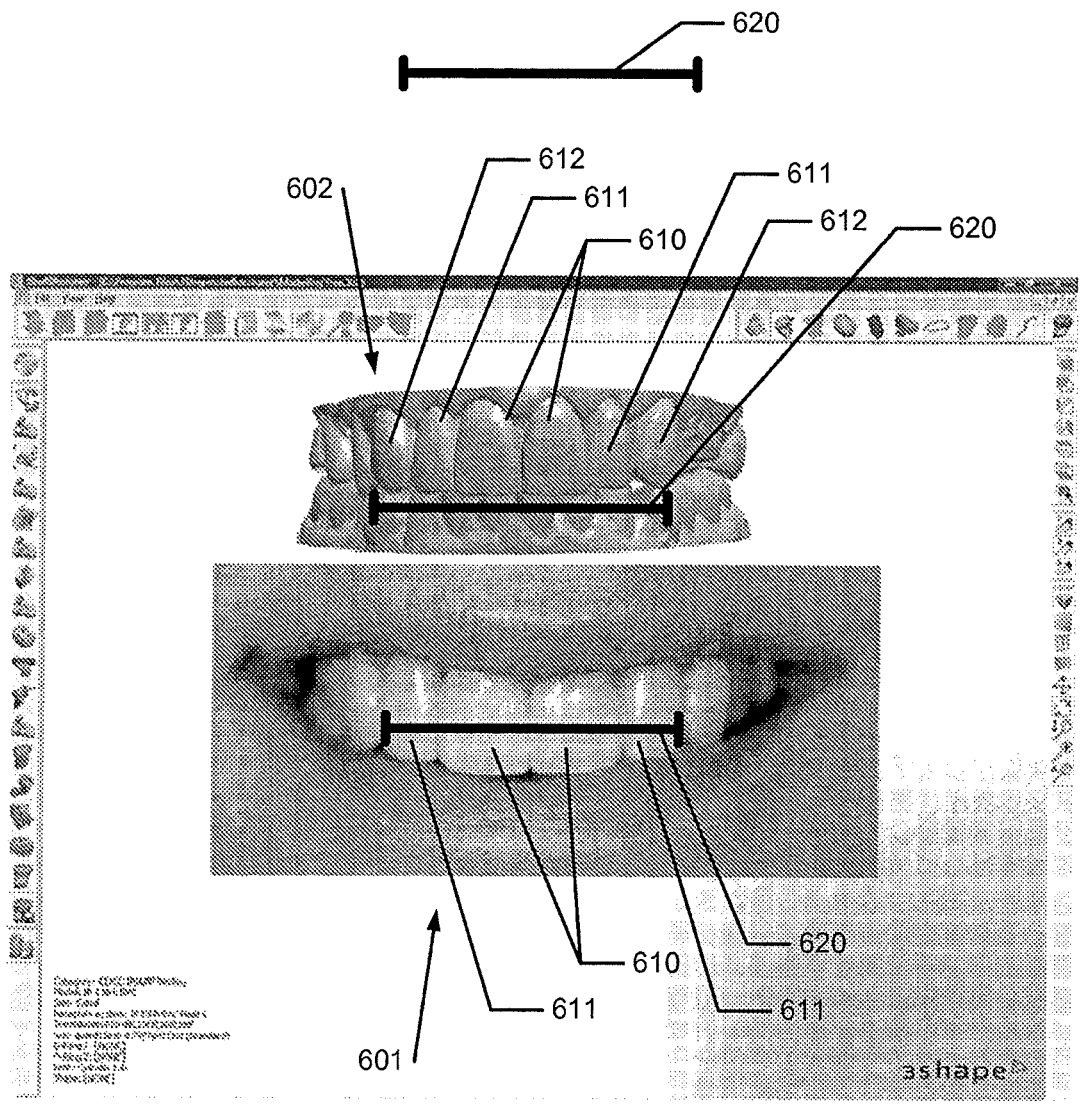

FIG. 6b) shows an example where a virtual action for arrangement such as scaling is performed using a virtual measurement bar 620. The virtual measurement bar 620 is seen on both the 2D image 601 and the 3D model 602. On the 2D image 601, the measurement bar 620 has a length corresponding to the length across the upper two centrals 610 and the two laterals 611. However, on the 3D model, the measurement bar 620 has a length corresponding to both the upper two centrals 610, the two laterals 611 and the two cuspids 612. Thus in order to have matching sizes of the 2D image 601 and the 3D model 602, the 3D model should be scaled up or enlarged to fit the size of the 2D image.

Alternatively and/or additionally, the user can perform virtual actions of arrangement of the 2D digital image and/or of the 3D virtual model by means of eye measure.

Figure 7:
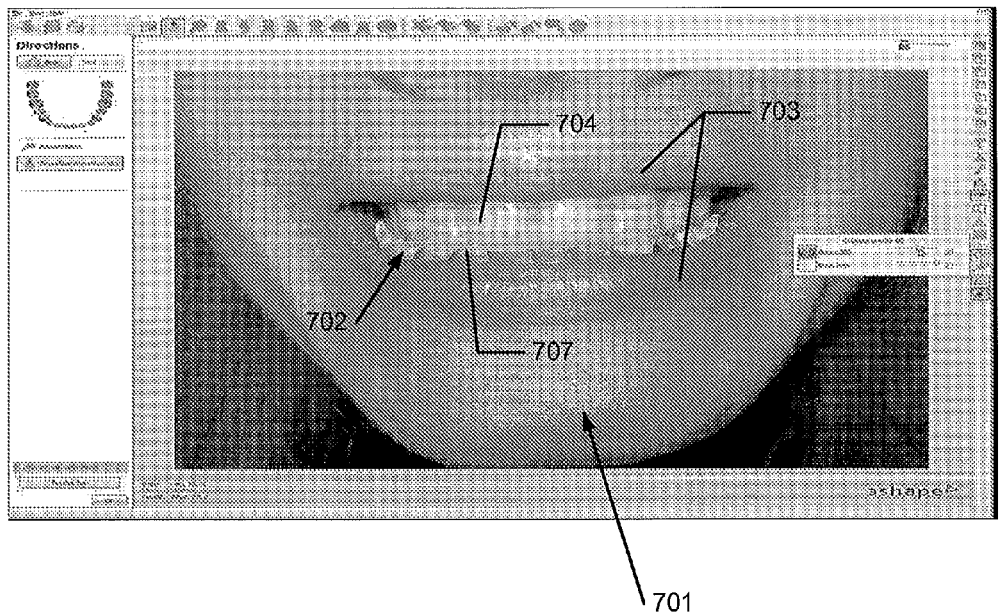
FIG. 7 shows an example of visualizing and arranging a 2D image and a 3D model.

FIG. 7 shows an example of visualizing and arranging a 2D image and a 3D model.

FIG. 7 shows a screen shot from a user interface in which both a 2D image 701 and a 3D model 702 of teeth are seen simultaneously. The 2D image 701 is a photograph of a part of a patients face comprising facial features in the form of the patient's lips 703 and the patient's existing upper teeth 704 behind the lips. In the place of the lower teeth on the 2D image the 3D model comprising the lower teeth 707 is arranged.

The 3D model 702 is arranged and aligned relative to the 2D image 701.

A restoration on the 3D model can be modeled to fit the facial features in the 2D image such as the patient's lips, the upper anterior teeth etc.

Figure 8:
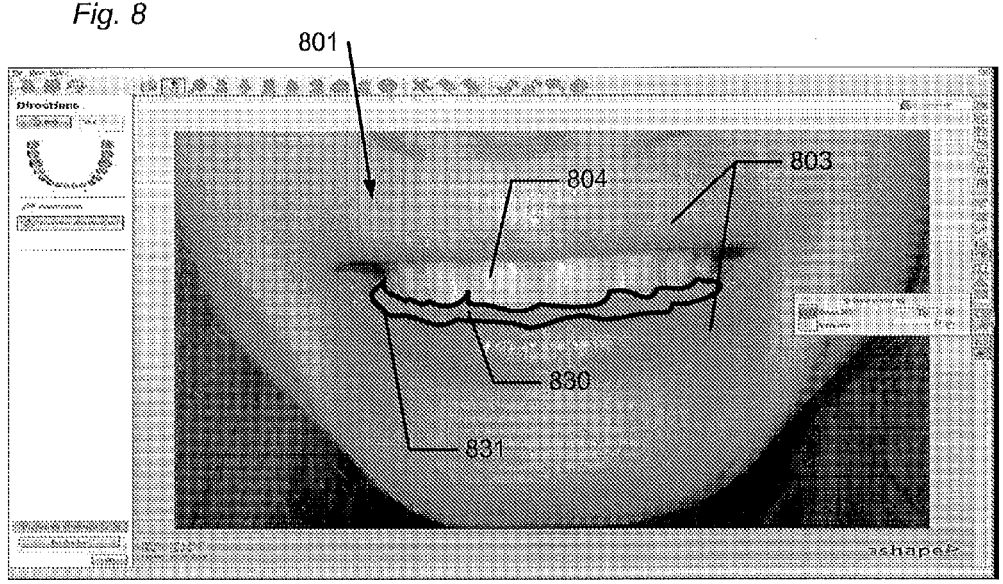
FIG. 8 shows an example of how a 3D model can be arranged in a 2D image, or how a 2D image can be laid over a 3D model.

FIG. 8 shows an example of how a 3D model can be arranged in a 2D image, or how a 2D image can be laid over a 3D model.

FIG. 8 shows a screen shot from a user interface in which a 2D image 801 is seen. The 2D image 801 is a photograph of a part of a patients face comprising the patient's lips 803 and the patient's existing upper teeth 804 behind the lips.

If a 3D model of teeth should be arranged in the place of the lower teeth, the area of the lower teeth in the 3D image can be marked and hidden or deleted by means of a non-transparent area 830. The marked area 830 can be marked by drawing a line 831 along the edge of the upper teeth and the lower lips. The marking of the line 831 can be performed automatically by means of automatic contour and/or color detection of the 2D image. Alternatively and/or additionally, the operator can draw the line 831 or otherwise mark the area 830.

The same may apply if more or less, e.g. all the teeth in the 2D image should be replaced with the teeth of a 3D model.

Figure 9:
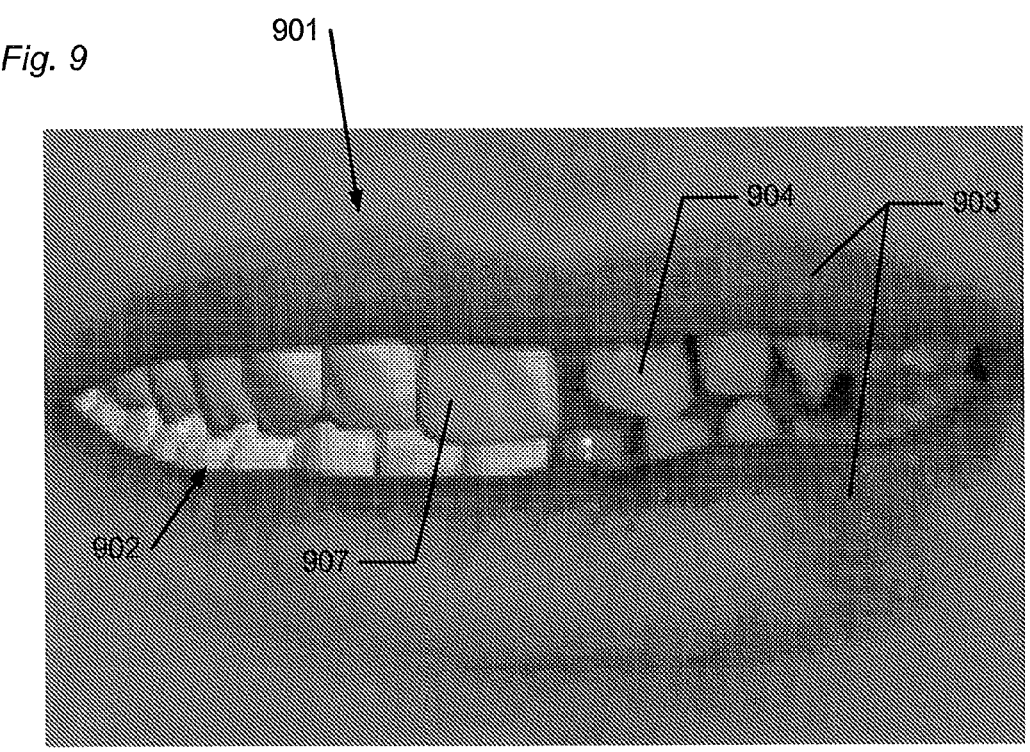
FIG. 9 shows an example of a before-and-after visualization.

FIG. 9 shows an example of a before-and-after visualization.

A before-and-after visualization can be obtained by continuously interchanging between situation views through gradual fading in-and-out, whereby technicians, dentists and patients are easily able to detect even the smallest alterations and smile details for optimal comparisons.

FIG. 9 shows an example in which both a part of a 2D image 901 and part of a 3D model 902 of teeth are seen simultaneously. The 2D image 901 is a photograph of a part of a patients face comprising facial features in the form of the patient's lips 903 and the patient's existing teeth 904 behind the lips. In the place of the lower and upper teeth in the left side of the patient's mouth (right side for the patient) the 3D model comprising teeth 907 is seen.

The 3D model 902 is arranged and aligned relative to the 2D image 901.

The existing teeth 904 in the 2D image 901 correspond to the situation before restoring one or more of the teeth. The 3D model 902 with restored teeth 907 corresponds to a possible situation after restoration of the teeth. Since the view can be interchanged between before and after visualization, e.g. by gradual fading in-and-out, the suggested changes can very clearly be seen and evaluated.

Figure 10:
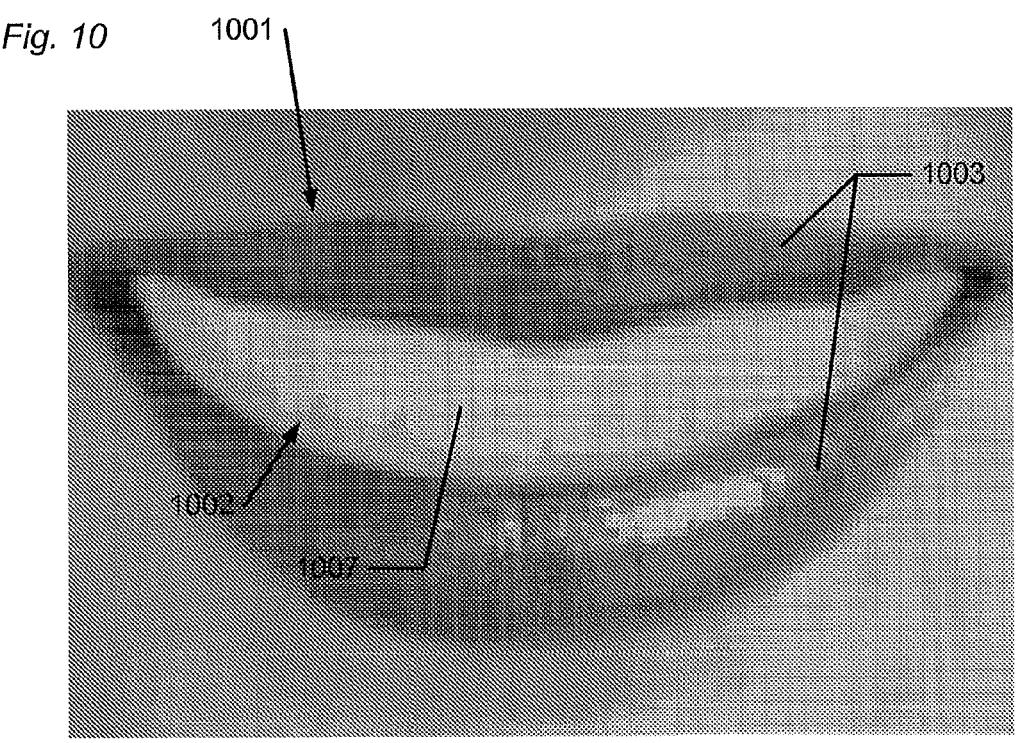
FIG. 10 shows an example of rendering of a 3D model of teeth arranged relative to a 2D image.

FIG. 10 shows an example of rendering of a 3D model of teeth arranged relative to a 2D image.

FIG. 10 shows an example in which both a 2D image 1001 and a 3D model 1002 of teeth are seen simultaneously. The 2D image 1001 is a photograph of a part of a patients face comprising the patient's lips 1003. In the place of the teeth in the 2D image, a 3D model comprising modeled and rendered restored teeth 1007 is arranged. The restored teeth 1007 in the 3D model have been rendered, such as a photo-realistic rendering.

FIG. 11 shows an example of aligning a 2D image and a 3D virtual model relative to each other, cutting out the mouth and teeth of the 2D image to see the 3D virtual model in place of the teeth, and designing a restoration on the 3D virtual model based on the 2D image.

FIG. 11 shows a number of steps which may be performed for designing a restoration, but it should not be understood that all these steps should be performed for designing a restoration. In some cases aligning the 2D image and the 3D virtual model can be performed differently than shown in the FIG. 11, and in some cases the mouth and teeth is not cut out of the 2D image as shown in the FIG. 11.

Figure 11A:
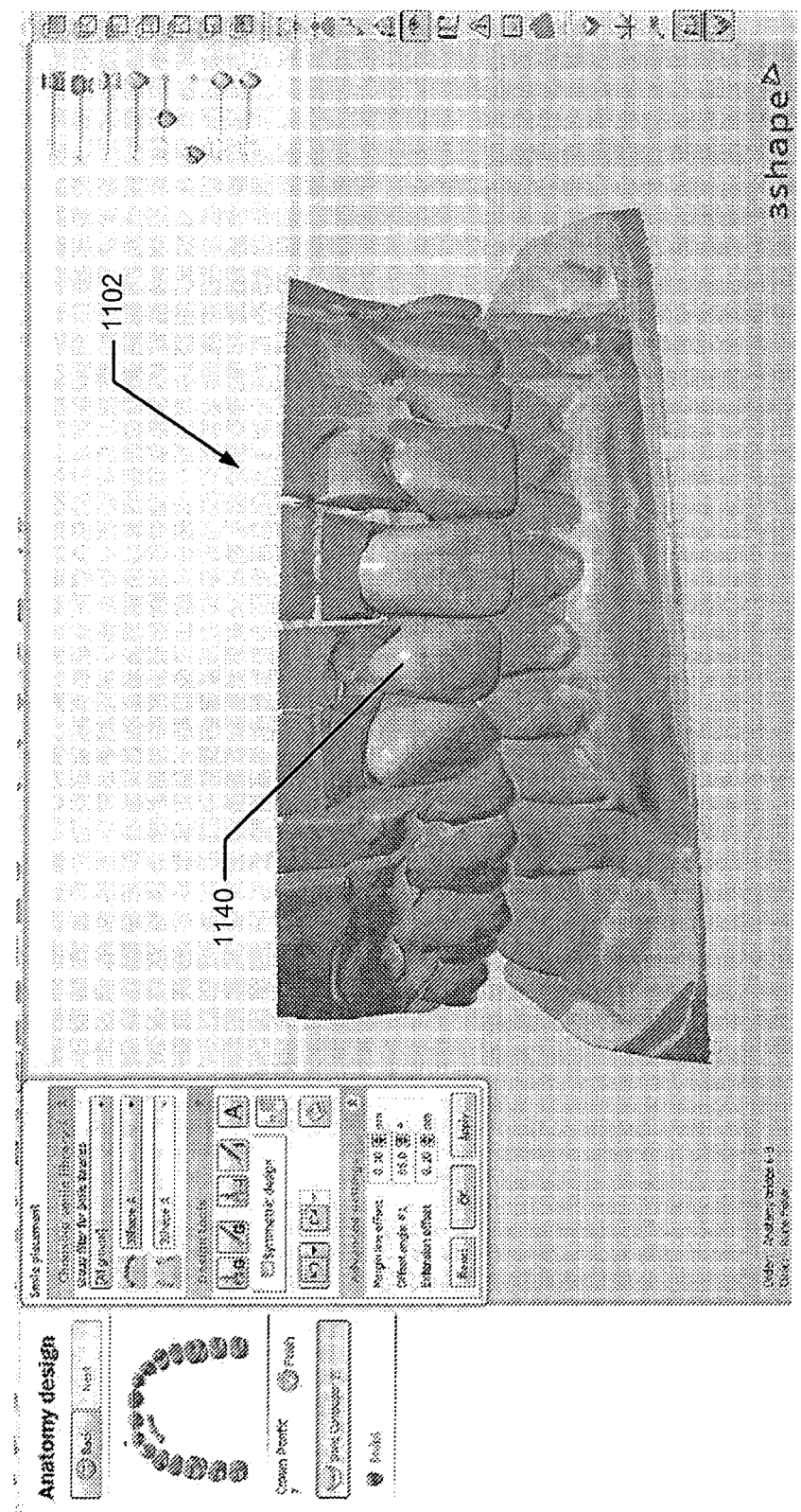
FIGS. 11A-11K show an example of aligning a 2D image and a 3D virtual model relative to each other, cutting out the mouth and teeth of the 2D image to see the 3D virtual model in place of the teeth, and designing a restoration on the 3D virtual model based on the 2D image.

FIG. 11*a*) shows a 3D virtual model 1102 of a patient's set of teeth. A first design of the restoration 1140 in the form of a bridge comprising three teeth is designed. The restoration is white whereas the original teeth in the 3D model are brown/grey in the figure.

Figure 11B:
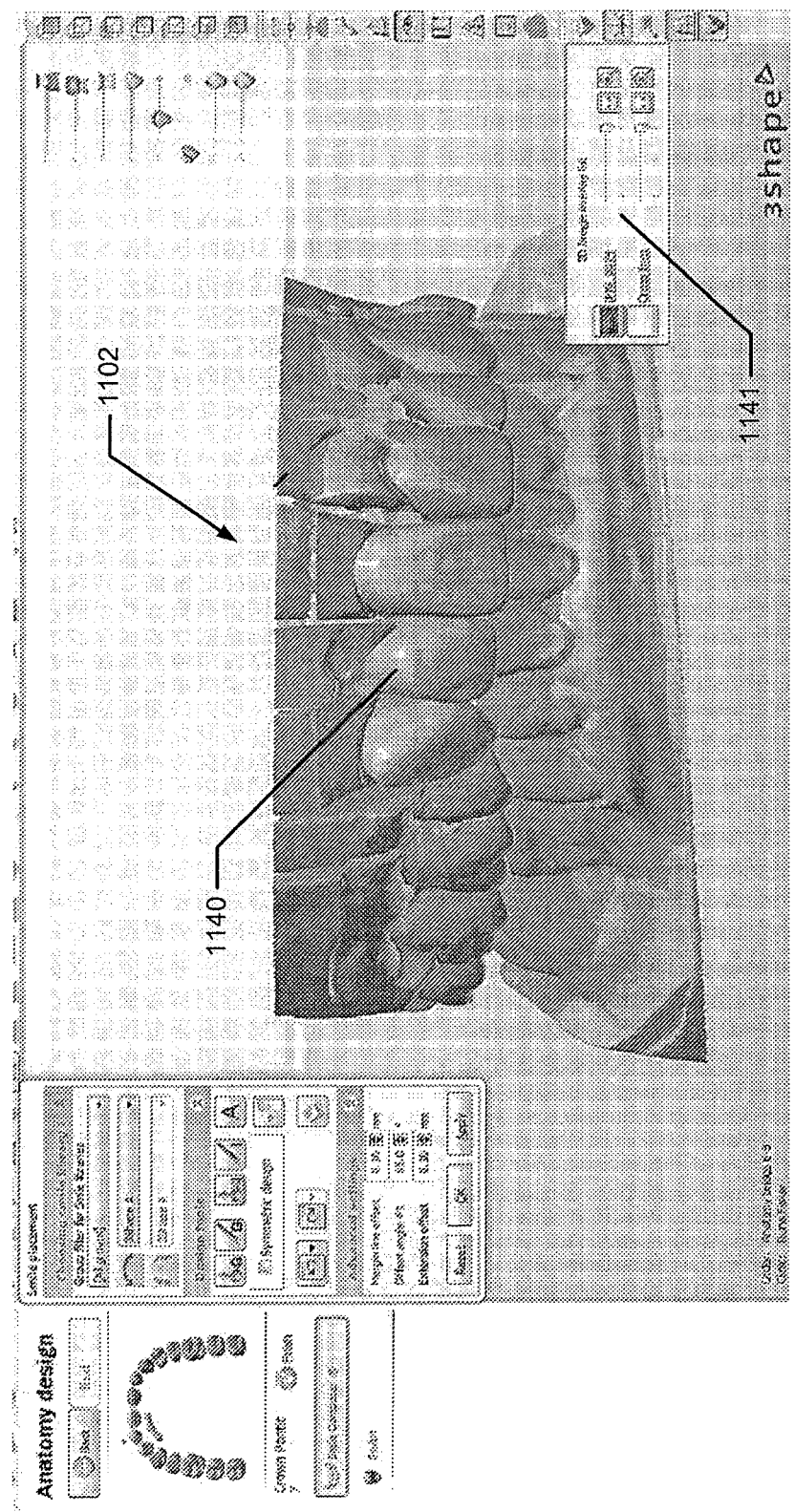

FIG. 11*b*) shows the 3D model 1102 with the restoration 1140. In the lower right corner a menu 1141 is shown which allows the user to select a 2D image to overlay on the 3D model 1102.

Figure 11C:
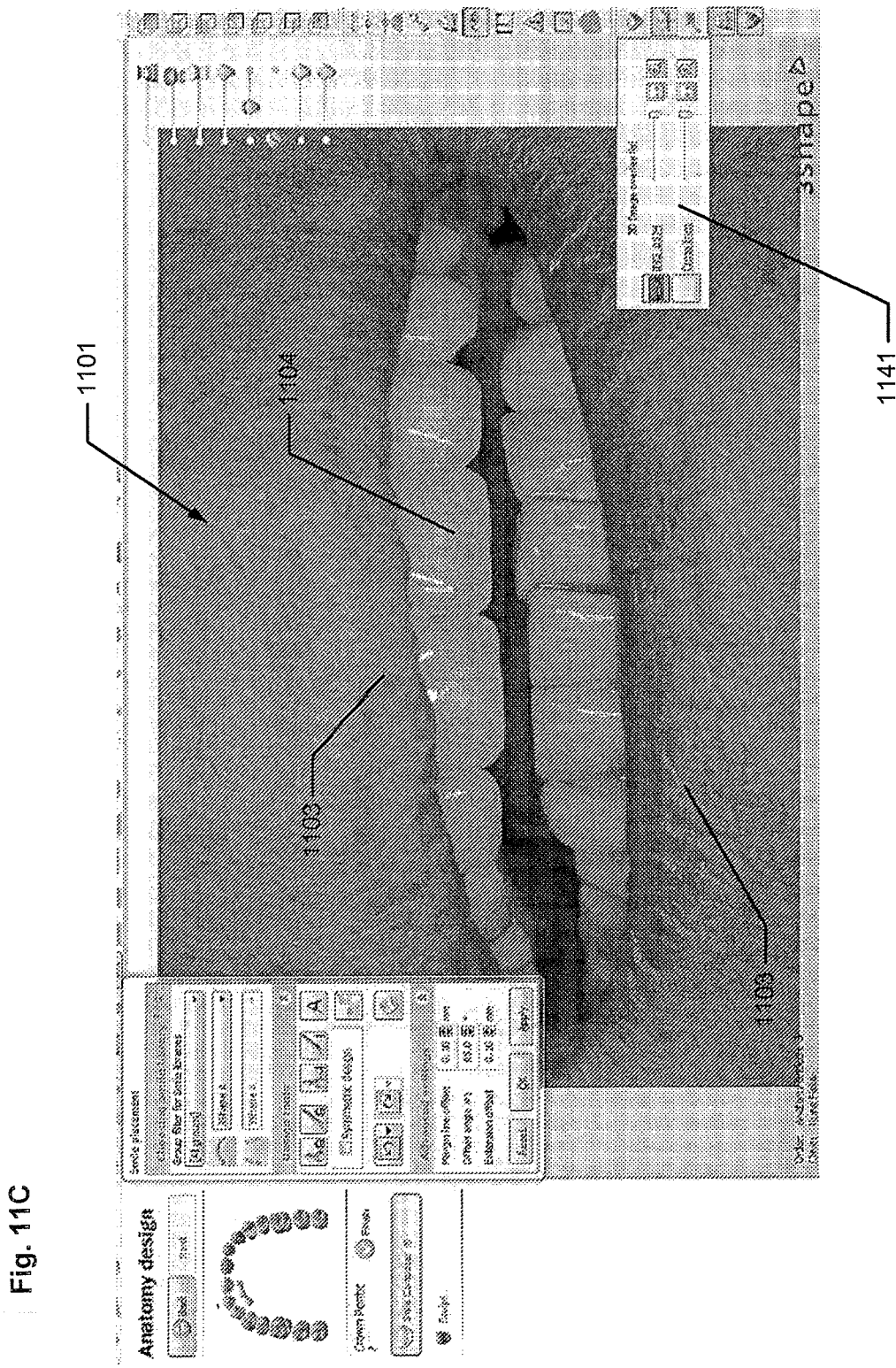

FIG. 11*c*) shows a 2D image 1101 of the patient's lower face showing the mouth including lips 1103 and existing teeth 1104. The menu 1102 is also seen in the lower right corner.

Figure 11D:
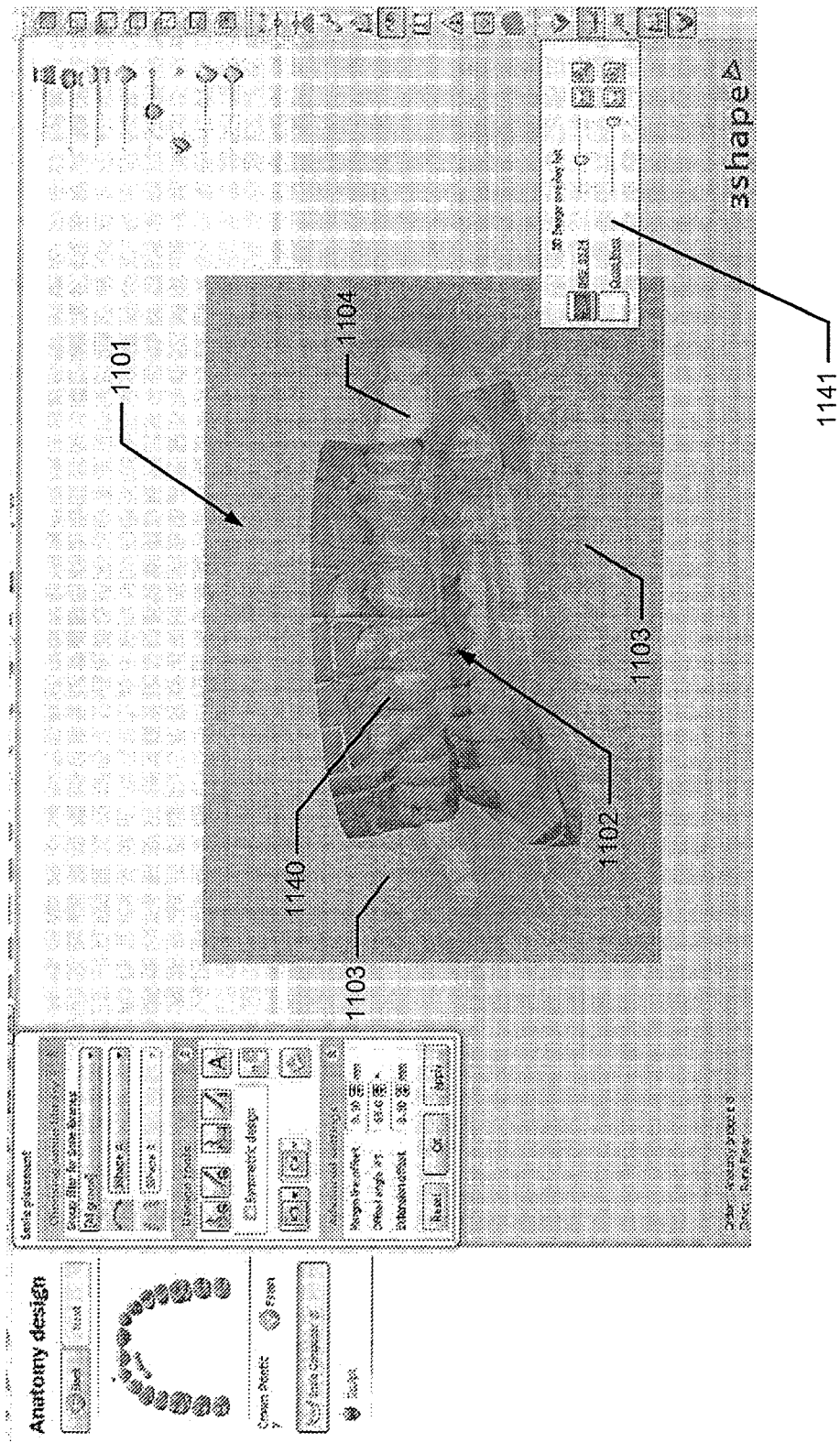

FIG. 11*d*) shows both the 2D image 1101 with lips 1103 and teeth 105, and the 3D virtual model 1102 with the restoration 1140. The 2D image 1101 has been made partially transparent such that both the 2D image and the 3D virtual model can be seen. A scale on the menu 1141 in the lower right corner can be changed to adjust the transparency of the 2D image and/or the 3D model.

Figure 11E:
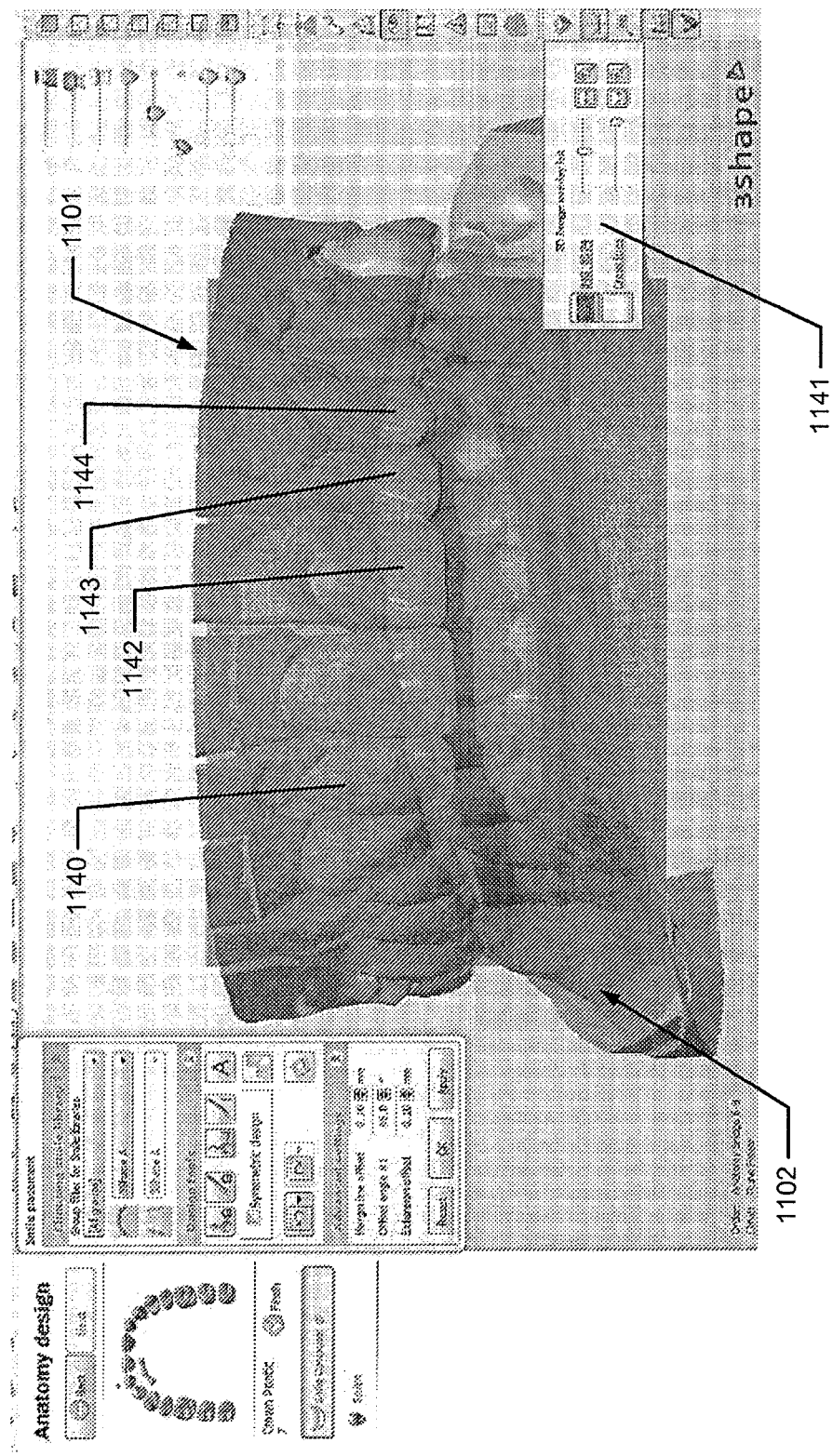

FIG. 11*e*) shows the 2D image 1101 and the 3D virtual model, where the 2D image has been made partially transparent, such that both the 2D image and the 3D virtual model can be seen. The 2D image and the 3D virtual model have been aligned which can be seen in that the incisal edge of the three anterior teeth 1142, 1143 and 1144 matches on the 2D image and the 3D virtual model.

Furthermore, it can be seen that the first design of the restoration 1140 has been designed such that the new teeth in the restoration 1140 are a little bit shorter than the original teeth on the 2D image.

The patient may have required the restoration 1140 because the original teeth was broken, damaged, dead, caused problems with the occlusion, problems with the gingival etc.

Figure 11F:
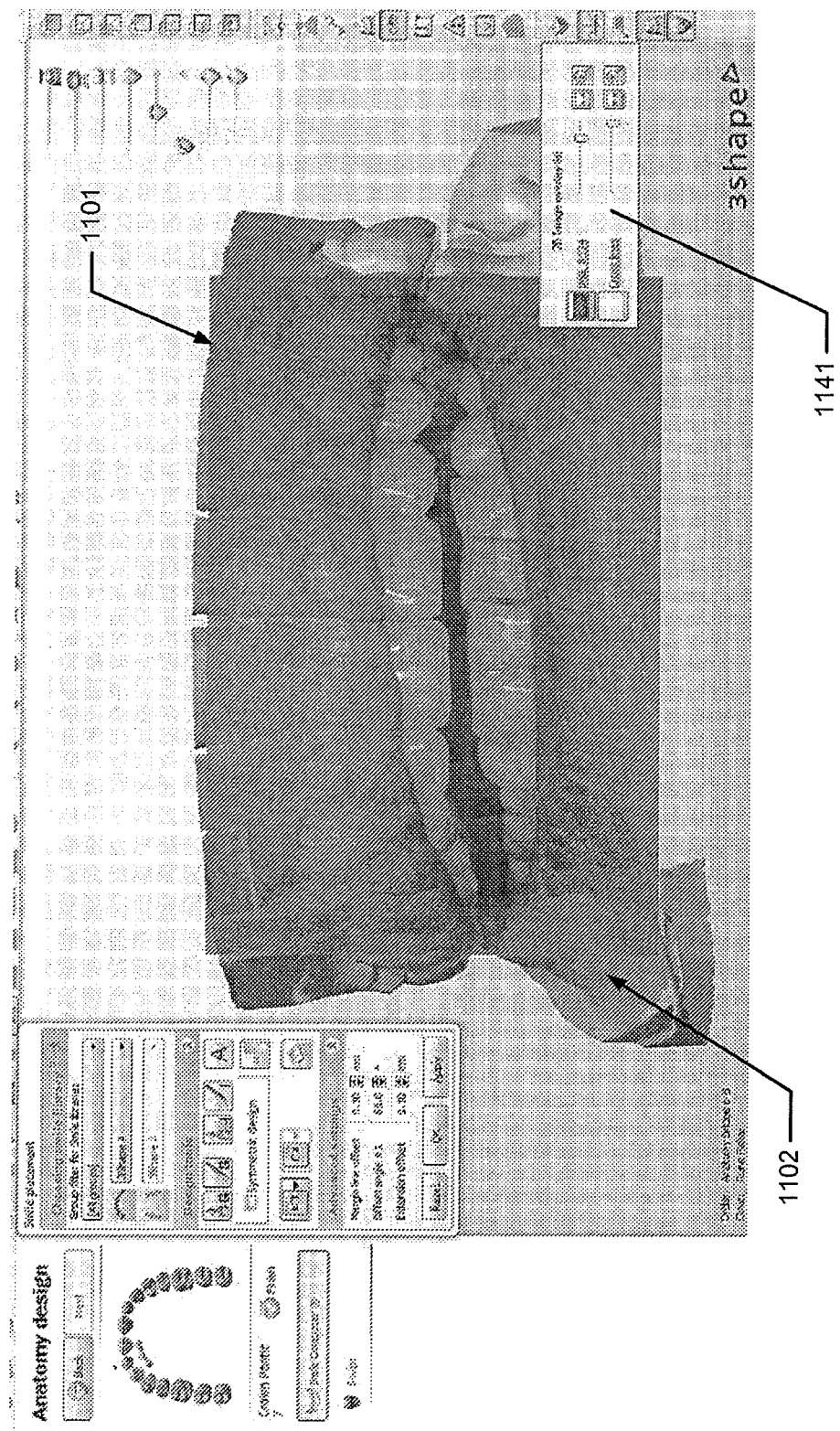

FIG. 11*f*) shows the 2D image 1101 and the 3D virtual model 1102, where the transparency of the 2D image is a little bit different compared to the transparency in FIG. 11*e*). In FIG. 11*f*) the 2D image is less transparent than in FIG. 11*e*). The transparency can be adjusted by means of the scale on the menu 1141.

Figure 11G:
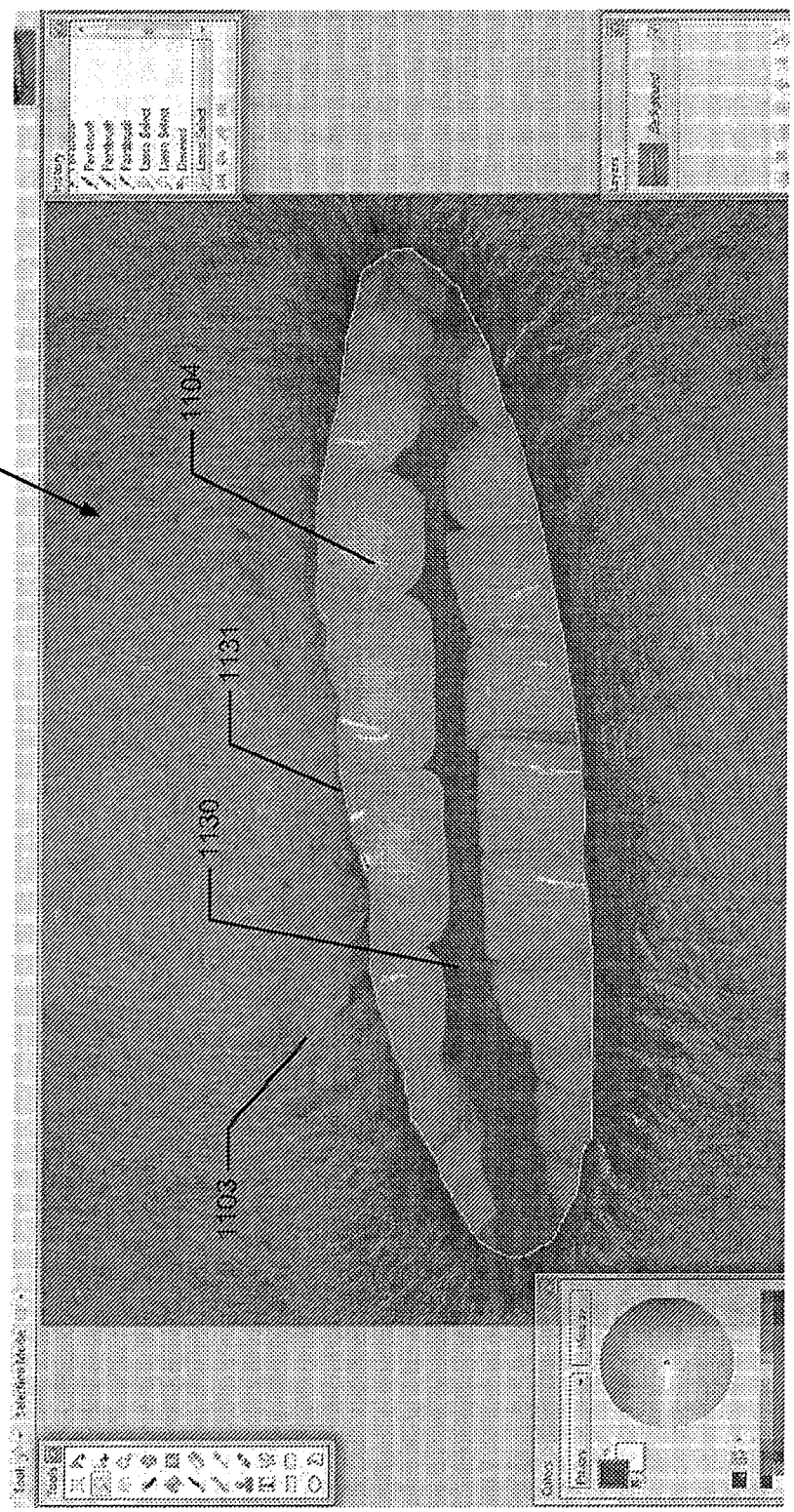

FIGS. 11*g*), 11*h*) and 11*i*) show an example of virtually cutting out teeth of the 2D image.

FIG. 11*g*) shows the 2D image 1101 of the patient's lower face where the lips 1103 and the teeth 1104 can be seen. The line 1131 along the lips 1103 is marked and thereby the whole area 1130 within the lips can be marked.

Figure 11H:
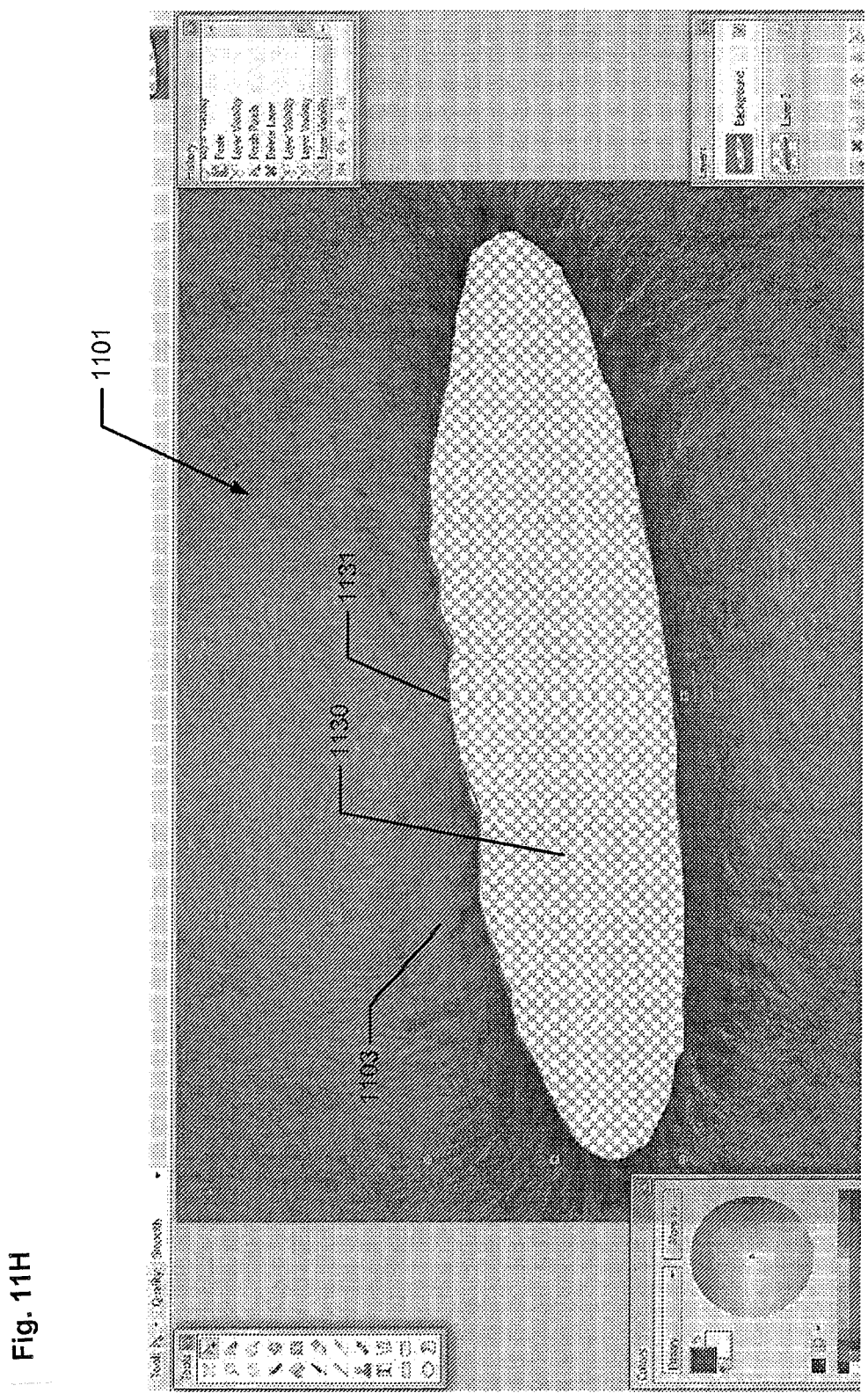

FIG. 11*h*) shows the 2D image 1101 where the area 1130 within the line 1131 along the lips 1103 has been emptied, i.e. replaced with an empty space, a blank area etc. Thus the teeth 1104 in the area 1130 is removed from view, deleted, disregarded etc. The area 1130 has been made transparent such that the 3D virtual model arranged behind the 2D image can be seen in the area 1130.

Figure 11I:
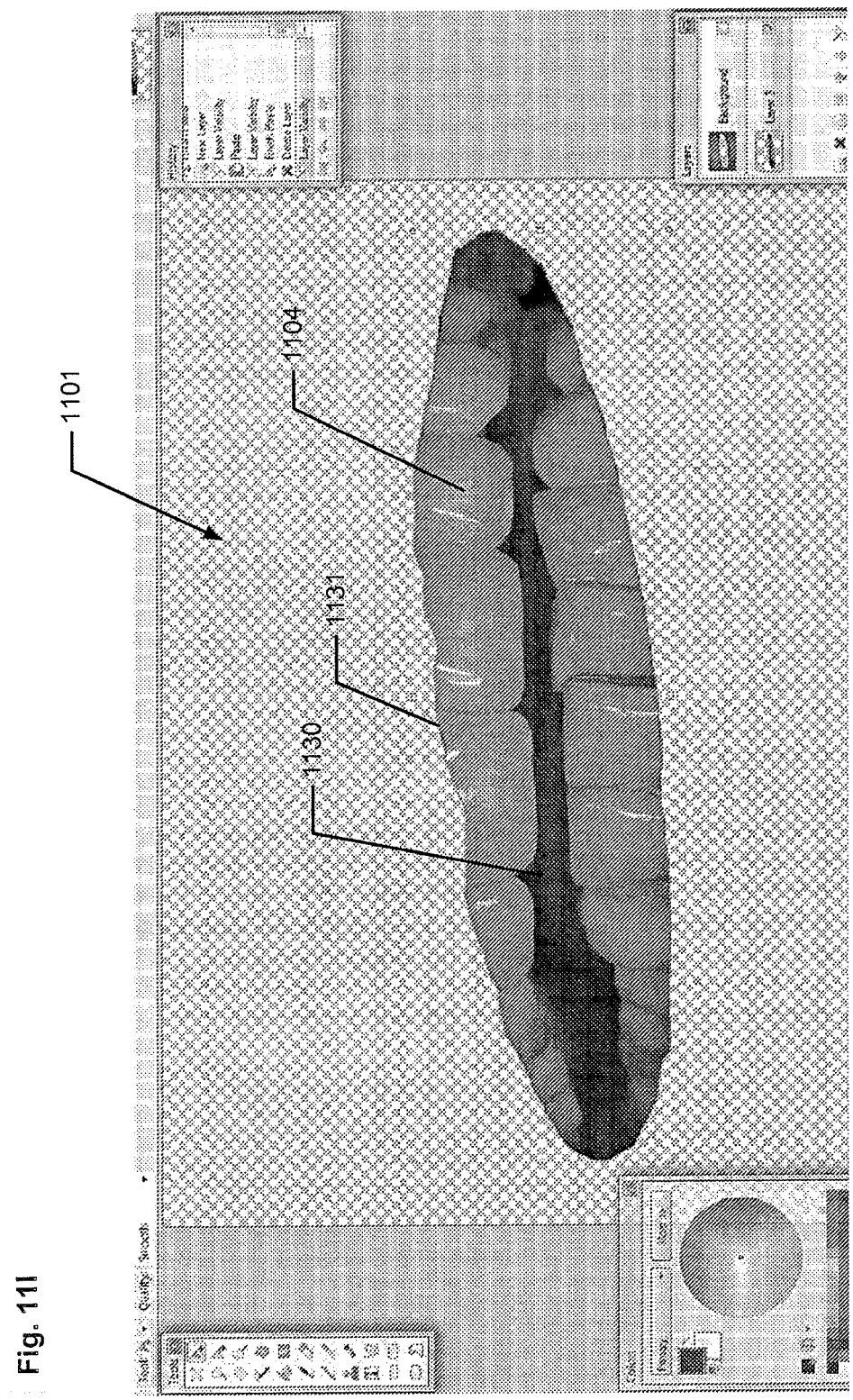

FIG. 11*i*) shows the area 1130 which is the part of the 2D image 1101 within the line 1131 along the lips. Thus the teeth 1104 are seen in this cut-out part of the 2D image.

Figure 11J:
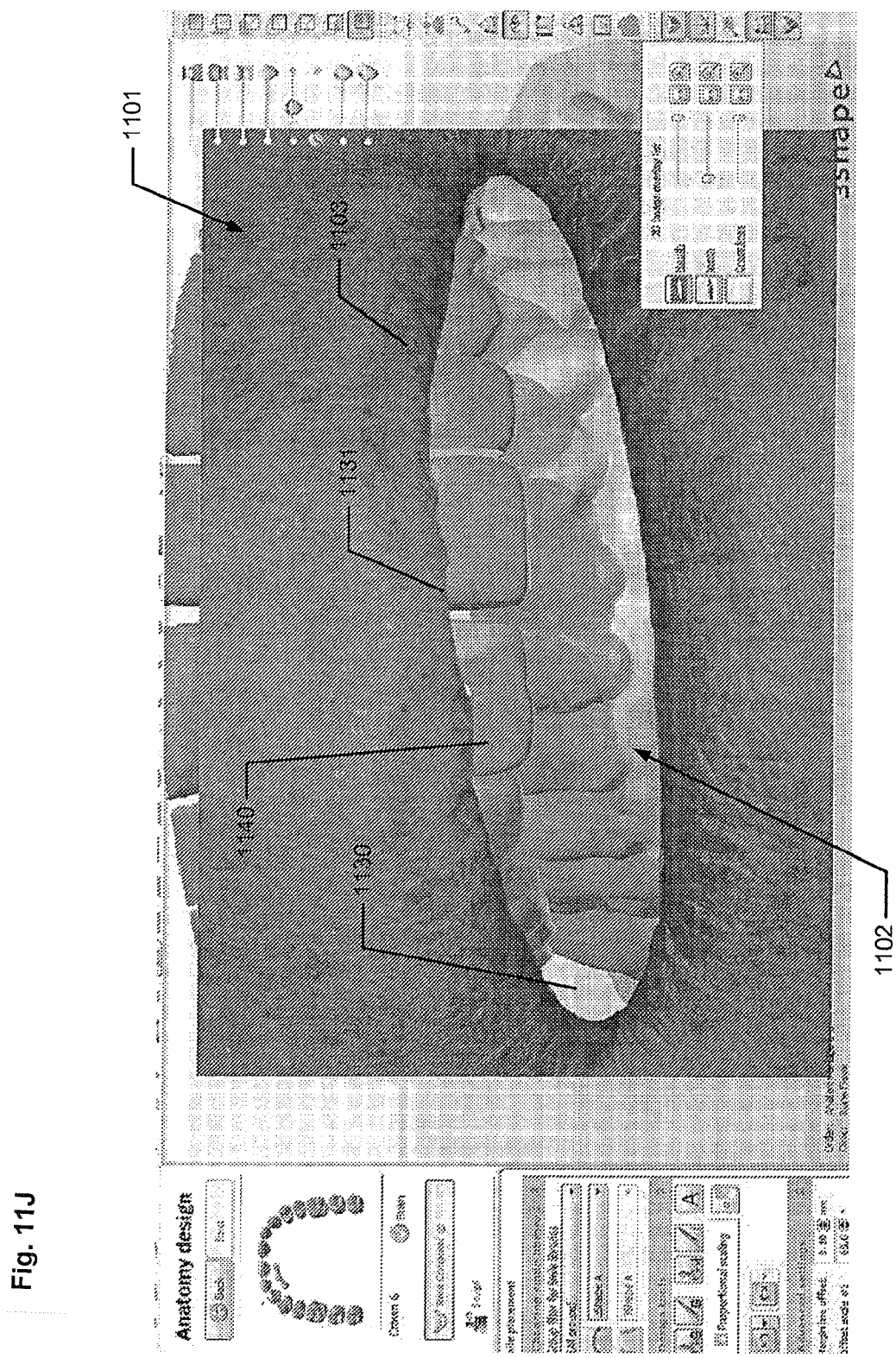

FIG. 11*j*) shows the 2D image 1101 with the cut-out area 1130 along the line 1131 of the lips 1103, and the 3D virtual model 1102 is now visible in the cut-our area 1130 of the 2D image. The restoration 1140 of the 3D model 1102 is seen, and it can be seen that the restoration 1140 has not been finally designed yet, as there is a rather large gap between the upper central teeth, where the left central tooth (as seen for the viewer, but the right central tooth) is part of the restoration 1140.

Figure 11K:
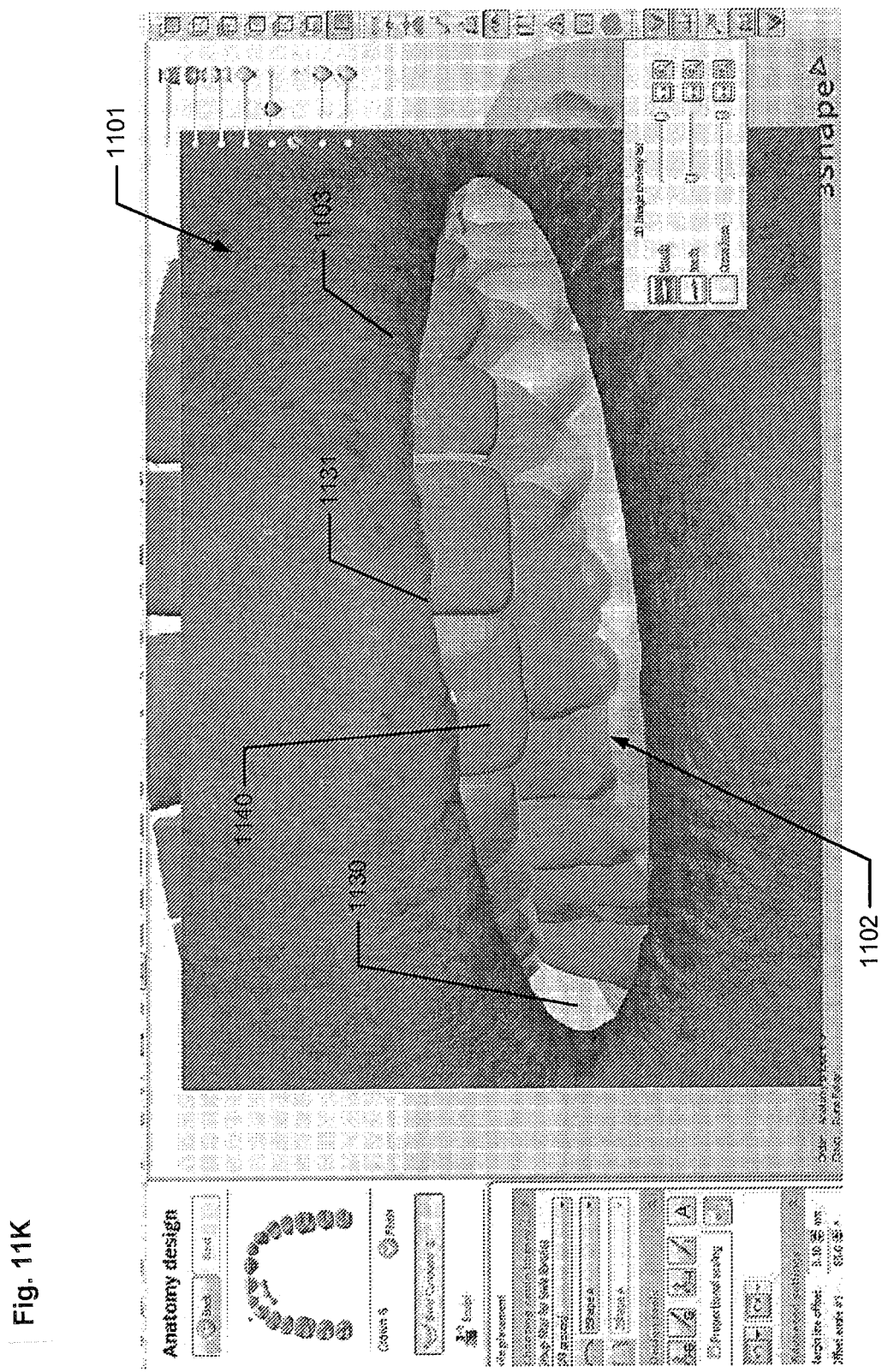

FIG. 11*k*) shows that the restoration 1140 has now been finally designed, since the restoration 1140 has been designed such that there is no big gap between the two central upper teeth. Thus the restoration 1140 has been designed based on and designed to match and fit facial features seen on the 2D image, such as the lips 1103.

In this case where the restoration is three of the upper anterior teeth, the restoration is partly designed also to be symmetrical with the corresponding teeth in the other side of the upper jaw. But in cases where e.g. the restoration is a full denture or the restoration is all the anterior teeth in e.g. the upper jaw, then the new teeth in the restoration can be designed to match and fit the facial features of the patient's face as seen on the 2D image, and the restoration may not be designed to be symmetrical with any existing teeth in the patient's mouth.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

When a claim refers to any of the preceding claims, this is understood to mean any one or more of the preceding claims.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

The invention claimed is:

1. A computer-implemented method of designing a dental restoration for a patient, wherein the method comprises: using a hardware processor to:
provide one or more 2D images, where at least one of the one or more 2D images comprises at least one facial feature, wherein the at least one facial feature comprises lips,
either virtually cut at least a part of teeth out of the at least one 2D image or render a part of the at least one 2D image that includes teeth at least partly or wholly transparent;
provide a 3D virtual model of at least part of an oral cavity of the patient;
arrange the at least one 2D image relative to the 3D virtual model in a virtual 3D space such that the at least one 2D image and the 3D virtual model are aligned when viewed from a viewpoint and remain separate representations after being arranged, whereby the 3D virtual model and the at least one 2D image are both visualized in the 3D space; and
design a restoration for the 3D virtual model, where the restoration is designed to fit the at least one facial feature of the at least one 2D image;
wherein the at least one 2D image and the 3D virtual model are aligned by scaling, translating or rotating the at least one 2D image or the 3D virtual model relative to each other.

2. The method according to claim 1, wherein facial features are present in an image of the patient or in a generic image of a person.

3. The method according to claim 1, wherein the at least one facial feature comprises one or more imaginary lines of a face in the at least one 2D image.

4. The method according to claim 1, wherein the design of the restoration is performed to automatically fit the at least one facial feature of the at least one 2D image, and the 2D image is digital.

5. The method according to claim 1, wherein the at least one 2D image and the 3D virtual model are aligned based on one or more unprepared teeth.

6. The method according to claim 1, wherein the hardware processor is used to provide two 3D virtual models, where the first 3D virtual model comprises at least one prepared tooth and the second 3D virtual model comprises no prepared teeth, and where the first and the second 3D virtual models are aligned.

7. The method according to claim 6, wherein the at least one 2D image and the second 3D virtual model comprising no prepared teeth are aligned.

8. The method according to claim 7, wherein the at least one 2D image and the first 3D virtual model comprising at least one prepared tooth are aligned based on the alignment between the first and the second 3D virtual model and based on the alignment between the at least one 2D image and the second 3D virtual model.

9. The method according to claim 1, wherein the hardware processor is used to virtually cut at least a part of teeth out of the at least one 2D image wherein at least the lips remain to be visible in the at least one 2D image.

10. The method according to claim 1, wherein the hardware processor is used to cut out a part of the at least one 2D image which is inside an edge of the lips.

11. The method according to claim 1, wherein an edge of the lips is marked on the at least one 2D image.

12. The method according to claim 1, wherein a silhouette of a biting edge of at least upper anterior teeth on the at least one 2D image and on the 3D virtual model is used to perform the alignment of the at least one 2D image and the 3D virtual model.

13. The method according to claim 1, wherein the hardware processor is used to scale the at least one 2D image and the 3D virtual model to show at least part of teeth in a same size.

14. The method according to claim 1, wherein the hardware processor is used to section at least two or more teeth in the 3D virtual model or in the at least one 2D image.

15. The method according to claim 1, wherein the alignment of the 3D virtual model and the at least one 2D image for one or more perspective views is performed by interpolation or extrapolation of other perspective views.

16. The method according to claim 1, wherein arrangement comprises one or more virtual actions, wherein the virtual actions for arrangement comprise rotations and translations left/right and back/forth of the at least one 2D image or of the 3D virtual model.

17. The method according to claim 1, wherein texture from the at least one 2D image is mapped onto the 3D virtual model or the restoration.

18. The method according to claim 1, wherein the method further comprises changing a perspective view of the at least one 2D image or of the 3D virtual model to obtain a same perspective view.

19. The method according to claim 18, wherein the method comprises determining an angle of the perspective view.

20. The method according to claim 18, wherein an angle of the 3D virtual model and the at least one 2D image is configured to adapt relative to the perspective view of the at least one 2D image.

21. The method according to claim 18, wherein the method further comprises de-warping the perspective view of the at least one 2D image for visually aligning the at least one 2D image and the 3D virtual model.

22. The method according to claim 1, wherein the at least one 2D image is retrieved from a library comprising a number of images of teeth.

23. The method according to claim 1, wherein the at least one 2D image is a template for supporting designing teeth of the patient.

24. The method according to claim 1, wherein the at least one 2D image shows a facial feature in the form of at least a number of front teeth.

25. The method according to claim 1, wherein the at least one 2D image is an X-ray image of teeth of the patient.

26. The method according to claim 1, wherein the at least one facial feature comprises teeth; and wherein the hardware processor is used to
   detect anatomical points on the teeth, where the anatomical points are present and detectable both on the one or more 2D images and the 3D virtual model, and
   perform virtual actions for arrangement based on corresponding anatomical points on the one or more 2D images and the 3D virtual model.

27. The method according to claim 1, wherein the designed restoration is configured for manufacturing a corresponding dental restoration.

28. A nontransitory computer readable medium encoded with a computer program for causing a data processing system to perform the method of claim 1, when said program code is executed on the data processing system.

29. A system for designing a dental restoration for a patient, wherein the system comprises:
   a hardware processor configured to:
      provide one or more 2D images, where at least one of the one or more 2D images comprises at least one facial feature, wherein the at least one facial feature comprises lips;
      either virtually cut at least a part of teeth out of the at least one 2D image or render a part of the at least one 2D image that includes teeth at least partly or wholly transparent;
      provide a 3D virtual model of at least part of an oral cavity of the patient;
      arrange the at least one 2D image relative to the 3D virtual model in a virtual 3D space wherein the at least one 2D image and the 3D virtual model are aligned when viewed from a viewpoint and remain separate representations after being arranged, and wherein the 3D virtual model and the at least one 2D image are both visualized in the 3D space; and
      design a restoration for the 3D virtual model, where the restoration fits the facial feature of the at least one 2D image;
   wherein the at least one 2D image and the 3D virtual model are aligned by scaling, translating or rotating the at least one 2D image or the 3D virtual model relative to each other.

30. The system according to claim 29, wherein the designed restoration is configured for manufacturing a corresponding dental restoration.

* * * * *